(12) United States Patent
Nelson et al.

(10) Patent No.: US 7,214,498 B2
(45) Date of Patent: May 8, 2007

(54) TUMOR ASSOCIATED ANTIGENS AND METHODS OF USING THE SAME

(75) Inventors: Brad H. Nelson, Seattle, WA (US); Bradley C. Stone, Seattle, WA (US)

(73) Assignee: Benaroya Research Institute at Virginia Mason, Seattle, WA (US)

( * ) Notice: Subject to any disclaimer, the term of this patent is extended or adjusted under 35 U.S.C. 154(b) by 548 days.

(21) Appl. No.: 10/106,559

(22) Filed: Mar. 25, 2002

(65) Prior Publication Data

US 2007/0077556 A1    Apr. 5, 2007

Related U.S. Application Data

(60) Provisional application No. 60/278,237, filed on Mar. 24, 2001, provisional application No. 60/278,253, filed on Mar. 23, 2001.

(51) Int. Cl.
G01N 33/53 (2006.01)
(52) U.S. Cl. ............... 435/7.23; 436/501; 436/518
(58) Field of Classification Search ............... 435/7.23, 435/6; 436/501, 518
See application file for complete search history.

(56) References Cited

U.S. PATENT DOCUMENTS

| | | | |
|---|---|---|---|
| 5,652,115 A | 7/1997 | Marks et al. |
| 5,872,217 A | 2/1999 | Kuhajda et al. |
| 6,004,755 A | 12/1999 | Wang |
| 6,645,465 B2 | 11/2003 | Hanash et al. |
| 2001/0005582 A1 | 6/2001 | Benistant et al. |

FOREIGN PATENT DOCUMENTS

| | | |
|---|---|---|
| WO | WO99/00671 A2 | 1/1999 |
| WO | WO99/39210 | 8/1999 |
| WO | WO99/51772 | 10/1999 |
| WO | WO99/58978 A2 | 11/1999 |
| WO | WO2003/064593 A2 | 8/2003 |
| WO | WO2003/064593 A3 | 8/2003 |

OTHER PUBLICATIONS

Yanagidani et al., Journal of autoimmunity (ENGLAND) Aug. 2000, vol. 15, issue 1, p. 75-80.*
Voet et al., (1990, Biochemistry, John Wiley & Sons, p. 816 only).*
Joan Pontius, et al., UniGene, downloaded on Apr. 11, 2006 from NCBI website, created Oct. 9, 2002, and updated Aug. 13, 2003.*
Motfort-Cabello, 2004, Homeopathy, vol. 93, pp. 88-93, abstract only.*
Definition of "Malignant" the online dictionary downloaded from world wide web, m-w.com on Apr. 12, 2006.*
Cao et al., 1999, Breast Cancer Research and Treatment, vol. 53, pp. 279-290.*
Bast, Jr. et al., "Reactivity of a Monoclonal Antibody with Human Ovarian Carcinoma," *J. Clin. Invest.* 68:1331-1337 (Nov. 1981).

Bast, Jr. et al., "A Radioimmunoassay Using a Monoclonal Antibody to Monitor the Course of Epithelial Ovarian Cancer," *New England Journal of Medicine* 309:883-887 (Oct. 13, 1983).
Piver et al., "Epidemiology and Etiology of Ovarian Cancer," *Seminars in Oncology* 18:177-185 (Jun. 1991).
Einhorn et al., "Prospective Evaluation of Serum CA 125 Levels for Early Detection of Ovarian Cancer," *Obstetrics & Gynecology* 80:14-18 (Jul. 1992).
Disis et al., "Existent T-Cell and Antibody Immunity to HER-2/neu Protein in Patients with Breast Cancer," *Cancer Research* 54:16-20 (Jan. 1, 1994).
Berchuck et al., "The p53 tumor suppressor gene frequently is altered in gynecologic cancers," *Am. J. Obstet. Gynecol.* 170:246-252 (Jan. 1994).
Boring et al., "Cancer Statistics 1994," *CA-Cancer J. Clin.* 44:7-26 (Jan./Feb. 1994).
Orth et al., "Genetic instability in human ovarian cancer cell lines," *Proc. Natl. Acad. Sci USA* 91:9495-9499 (Sep. 1994).
Sahin et al., "Human neoplasms elicit multiple specific immune responses in the autologous host," *Proc. Natl. Acad. Sci. USA* 92:11810-11813 (Dec. 1995).
Flagiello et al., "Relationship between DNA methylation and gene expression of the *HOXB* gene cluster in small cell lung cancers," *FEBS Letters* 380:103-107 (1996).
Disis et al., "High-Titer HER-2/*neu* Protein-Specific Antibody Can Be Detected in Patients With Early-Stage Breast Cancer," *J. Clin. Oncol.* 15:3363-3367 (Nov. 1997).
Jager et al., "Simultaneous Humoral and Cellular Immune Response against Cancer-Testis Antigen NY-ESO-1: Definition of Human Histocompatibility Leukocyte Antigen (HLA)-A2 binding Peptide Epitopes," *J. Exp. Med.* 187:265-270 (Jan. 19, 1998).
Stockert et al., "A Survey of the Humoral Immune Response of Cancer Patients to a Panel of Human Tumor Antigens," *J. Exp. Med.* 187:1349-1354 (Apr. 20, 1998).
Grigola et al., "Mapping of topoisomerase II α epitopes recognized by autoantibodies in idiopathic pulmonary fibrosis," *Clin. Exp. Immunol.*, 114:339-346 (1998).
Krosl et al., "Cellular proliferation and transformation induced by HOXB4 and HOXB3 proteins involves cooperation with PBX1," *Oncogene* 16:3403-3412 (1998).
Tavassoli et al., "p53 antibodies in the saliva of patients with squamous cell carcinoma of the oral cavity," *Int. J. Cancer* 78:390-391 (1998).
Jacobs et al., "Screening for ovarian cancer: a pilot randomised controlled trial," *The Lancet* 353:1207-1210 (Apr. 10, 1999).

(Continued)

*Primary Examiner*—Misook Yu
(74) *Attorney, Agent, or Firm*—Townsend and Townsend and Crew LLP

(57) ABSTRACT

The present invention provides methods and compositions for the diagnosis of hyperproliferative disease and autoimmune disease. Tumor associated antigens, nucleic acids encoding them and antibodies to the tumor associated antigens are provided for the diagnosis of hyperproliferative disease, such as, for example, ovarian cancer, breast cancer, lung cancer, colorectal cancer, and other epithelial cancers, and for the diagnosis of autoimmune disease.

9 Claims, No Drawings

OTHER PUBLICATIONS

Disis et al., "Generation of Immunity to the HER-2/*neu* Oncogenic Protein in Patients with Breast and Ovarian Cancer Using a Peptide-based Vaccine," *Clin. Cancer Res.* 5:1289-1297 (Jun. 1999).

Hengstler et al., "Contribution of *c-erbB-2* and Topoisomerase IIα to Chemoresistance in Ovarian Cancer," *Cancer Res.* 59:3206-3214 (Jul. 1, 1999).

Golub et al., "Molecular Classification of Cancer: Class Discovery and Class Prediction by Gene Expression Monitoring," *Science* 286:531-537 (Oct. 15, 1999).

Gadducci et al., "Assessment of the Prognostic Relevance of Serum Anti-p53 Antibodies in Epithelial Ovarian Cancer," *Gynecologic Oncology* 72:76-81 (1999).

Schummer et al., "Comparative hybridization of an array of 21,500 ovarian cDNAs for the discovery of genes overexpressed in ovarian carcinomas," *Gene* 238:375-385 (1999).

Jarvinen et al., "Amplification and Deletion of Topoisomerase IIα Associate with ErbB-2 Amplification and Affect Sensitivity to Topoisomerase II Inhibitor Doxorubicin in Breast Cancer," *Am. J. Pathol.* 156:839-847 (Mar. 2000).

Jager et al., "Monitoring CD8 cell responses to NY-ESO-1: Correlation of humoral and cellular immune responses," *PNAS* 97:4760-4765 (Apr. 25, 2000).

Baldwin et al., "*BRCA1* Promoter Region Hypermethylation in Ovarian Carcinoma: A Population-based Study," *Cancer Research* 60:5329-5333 (Oct. 1, 2000).

Abendstein et al., "Clinical Significance of Serum and Ascitic p53 Autoantibodies in Epithelial Ovarian Carcinoma," *Cancer* 1432-1437 (2000).

Bodey et al., "Immunocytochemical Detection of the Homeobox B3, B4, and C6 Gene Products in Breast Carcinomas," *Anticancer Res.* 20:3281-3286 (2000).

Disis et al., "Pre-existent immunity to the HER-2/neu oncogenic protein in patients with HER-2/neu overexpressing breast and ovarian cancer," *Breast Cancer Res. Treat.* 62:245-252 (2000).

Fishman et al., "Is Transvaginal Ultrasound Effective for Screening Asymptomatic Women for the Detection of Early-Stage Epithelial Ovarian Carcinoma?" *Gynecol. Oncol.* 77:347-349 (2000).

Vogl et al., "Autoimmunity against p53 predicts invasive cancer with poor survival in patients with an ovarian mass," *British J. Cancer* 83:1338-1343 (2000).

Wamakulasuriya et al., "Expression of p53 in oral squamous cell carcinoma is associated with the presence of IgG and IgA p53 autoantibodies in sera and saliva of the patients," *J. Pathol.* 192:52-57 (2000).

Welsh et al., "Analysis of gene expression profiles in normal and neoplastic ovarian tissue samples identifies candidate molecular markers of epithelial ovarian cancer," *PNAS* 98:1176-1181 (Jan. 30, 2001).

Thorsteinsdottir et al., "Defining Roles for *HOX* and *MEIS1* Genes in Induction of Acute Myeloid Leukemia," *Mol. Cell. Biol.* 21:224-234 (Jan. 2001).

Stone et al., "Proceeding of American Association for Cancer Research 2001," abstract No. 7583 (posted online on Feb. 27, 2001; mailed out in printed form on Mar. 10, 2001).

Ovarian Cancer—Internet Website: http://health.yahoo.com/health/Diseases_and_Conditions/Disease_Feed_Data/ovarian_cancer/ (printed Mar. 13, 2001).

Stages of Ovarian Cancer—Internet Website: http://health.yahoo.com/health/women/dealing5d.html (printed Mar. 13, 2001).

Imai et al., "Autoantibody to DNA Topoisomerase II in Primary Liver Cancer," *Clinical Cancer Research*, (Apr. 1995), vol. 1, pp. 417-424.

Zanaboni et al. "Tumor Antigen CA 125 as a Marker of Ovarian Epithelial Carcinoma," *Gynecol. Oncol.* 28:61-67 (1987).

Young et al., "*ERBB2* and Chromosome 17 Centromere Studies of Ovarian Cancer by Fluorescence In Situ Hybridization," *Genes, Chromosomes & Cancer* 16:130-137 (1996).

Hung and Satyaswaroop, "The Female Reproductive System: Cell Lines from Tumors of the Human Ovary and Uterus," in Hay et al., *Atlas of Human Tumor Cell Lines*, Academic Press, San Diego, pp. 359-386 (1994).

Tureci et al., "Serological analysis of human tumor antigens: molecular definition and implications," *Mol. Med. Today* 3:342-349 (Aug. 1997).

Afify et al., "HER-2/neu Oncogene Amplification in Stage I and Stage III Ovarian Papillary Serous Carcinoma," *Exp. Mol. Pathol.* 66: 163-169 (1999).

Tureci et al., "Exploitation of the Antibody Repertoire of Cancer Patients for the Identification of Human Tumor Antigens," *Hybridoma* 18:23-28 (1999).

Hattori et al., "DNA demethylase is expressed in ovarian cancers and the expression correlates with demethylation of CpG sites in the promoter region of c-erbB-2 and survivin genes," *Cancer Letters* 169:155-164 (2001).

Pettricoin III et al., "Use of proteomic patterns in serum to identify ovarian cancer," *The Lancet* 359:572-577 (Feb. 16, 2002).

\* cited by examiner

SEQUENCE LISTING

<160> NUMBER OF SEQ ID NOS: 18

<210> SEQ ID NO 1
<211> LENGTH: 2896
<212> TYPE: DNA
<213> ORGANISM: human

<400> SEQUENCE: 1

```
ctgatcagag ttattctgat ctgaagattt tgggcgttca aggcattaag ataatagcct      60
gagttgttca tggagttttt catcagtatg tctgaaacca ttaaatataa tgacgatgat     120
cataaaactc tgtttctgaa aacactaaat gaacaacgcc tggaaggaga attttgtgat     180
attgctattg tggttgagga tgtgaaattc agagcacaca gatgtgttct tgctgcctgc     240
agcacctact ttaaaaagct tttcaagaag cttgaggttg atagttcttc ggtcatagaa     300
atagattttc ttcgttctga tatatttgaa gaggtcctga actacatgta cacagcaaag     360
atttccgtga aaaagaaga tgttaactta atgatgtcat cgggtcagat tcttggtatc     420
cgattttggg ataaactgtg ttctcagaag cgtgatgtgt ccagtcccga tgaaaacaat     480
```

```
ggtcagtcca aaagtaagta ttgccttaaa ataaatcgcc ccattggaga tgctgctgac    540
acccaggatg atgatgtaga ggaaatcggg gatcaggatg acagtccttc tgatgacaca    600
gtagaaggca cacccccgag tcaggaggac ggcaagtcgc ccaccacaac gctcagggtt    660
caggaagcga tcctgaaaga gctggggagt gaggaagttc ggaaggtcaa ttgctacggc    720
caggaagtag aatccatgga gaccccagaa tcaaaagact tggggtccca gacccctcaa    780
gccttaacat ttaatgatgg gatgagtgaa gtgaaagatg aacagacacc aggctggaca    840
acagccgcca gtgacatgaa gtttgagtat ttgctttatg gtcaccatcg ggagcagatt    900
gcctgccagg cgtgtgggaa gacgttttct gatgaaggca gattgaggaa gcatgagaaa    960
ctccacacgg cggacaggcc atttgtttgt gaaatgtgca caaaggtttt caccacacag    1020
gcccacctga agaacacct aaaaatccac acaggatata agccctatag ctgtgaggtg    1080
tgtggaaaat catttatccg tgccccagac ttaaagaagc atgagagagt tcacagtaat    1140
gaaagaccgt ttgcgtgcca catgtgtgac aaagccttca acacaagtc tcacctcaag    1200 gatcatgaaa gaagacacag aggggaaaag ccttttgtgt gtggctcctg caccaaggca    1260
tttgccaagg catctgatct gaaaaggcac gagaacaata tgcacagtga aggaagcag    1320 gttaccccca gtgccatcca gagcgagaca aacagttgc aggcggcagc gatggctgcg    1380
gaagcagaac agcagctgga gacgatagcc tgtagctaga ggcggtggga cagggacact    1440
ttgcctggaa agtggagact gagatgacgt ggatcataat gagtgaatgc agttacaat    1500 attttgtgg aaacgtatga acattgtact cactggactt aaggcagtgc ttggttagct    1560
atttttaaga cttttcaagg aaatggtgtt cctcagttct gaccaaaccg tttcactgtc    1620
ttgtctggtg tctagtatta atgttgccag taagcacctc tctccctttt ttttttttta    1680 ttatttaat ttgagaactc ctgtgtccag tttagaagtg agagacttcc atttttagtt    1740
cctttacact caccacccta gcaagtgccc tgcacagagt aataagtaaa ttgatttcct    1800
aatcacaatt ctatgtgact tatggtcaaa agagcagttt taataacttt aaaagtactt    1860
cagatagacg cagaaaattg gtgagtggtt gaccaagaac actgcacaaa tataaaaaaa    1920
gttctggaaa tgcagaaggg cgttagattt atatttggtt tgttaatttt atatcactgt    1980
ttttcactgt ttttgtggac aaataatggt tgctttgctg aagtgttctt cctcaatctt    2040
gattgccctg tacctaccca aaagctgtag tcacacgtcc taaaggccaa gcaaacccac    2100
cgggatggtg gggggtcttg gagccaagct cttaggttcc tcttatttgg ggcagtacca    2160
gtccatacca gctgcgattt gtgagtggac ctgtggtaag aagaatagaa aaggctctca    2220
gagataaggt tttttacatg tgtaacaatc ccaagatttc ctagattaaa atcttaattg    2280
attttgaaat tggattttta tttagaatca aaattaggac aagaacagat aacttcttca    2340
gatacatttg tgtaaccttta cagaatgtca tcaagctttg gggctctgtg ggcacatga    2400 tttatccata aaggagatgc agtatgctta cttaaattaa taaatttaaa atcttttaag    2460
tgtgtaaata gtagtgttgg tcttacgtat tccaagtaaa aagtagacag ctgcactttt    2520
tttgcacatt ggattaaaat aacttccatc agcaacaaac atcagactgt ttttaacaaa    2580
tattaaagat tgtcagacca aatgtttatg ttttcgaaat atatttcatc actggttaca    2640
gttttaaata gaagttgatt gccttttcat agccgtaaat gagaattata aactctattc    2700
cagttttggt atactaaatg ttcttttaac catctttagg aatatattga aatgccaaca    2760
atagtttgaa ttgtgttctg taaaaaagta ttagtcaatt atttttcaaa atgtagaatt    2820
```

-continued

```
gtagaaaatg tcaattttc aaactcattt ttcattgcta ggatttcttt taaaaaaatt    2880
aaagtaattt cacttc                                                    2896
```

<210> SEQ ID NO 2
<211> LENGTH: 449
<212> TYPE: PRT
<213> ORGANISM: human

<400> SEQUENCE: 2

```
Met Glu Phe Phe Ile Ser Met Ser Glu Thr Ile Lys Tyr Asn Asp Asp
1               5                   10                  15

Asp His Lys Thr Leu Phe Leu Lys Thr Leu Asn Glu Gln Arg Leu Glu
            20                  25                  30

Gly Glu Phe Cys Asp Ile Ala Ile Val Val Glu Asp Val Lys Phe Arg
        35                  40                  45

Ala His Arg Cys Val Leu Ala Ala Cys Ser Thr Tyr Phe Lys Lys Leu
    50                  55                  60

Phe Lys Lys Leu Glu Val Asp Ser Ser Ser Val Ile Glu Ile Asp Phe
65                  70                  75                  80

Leu Arg Ser Asp Ile Phe Glu Glu Val Leu Asn Tyr Met Tyr Thr Ala
                85                  90                  95

Lys Ile Ser Val Lys Lys Glu Asp Val Asn Leu Met Met Ser Ser Gly
            100                 105                 110

Gln Ile Leu Gly Ile Arg Phe Leu Asp Lys Leu Cys Ser Gln Lys Arg
        115                 120                 125

Asp Val Ser Ser Pro Asp Glu Asn Asn Gly Gln Ser Lys Ser Lys Tyr
    130                 135                 140

Cys Leu Lys Ile Asn Arg Pro Ile Gly Asp Ala Ala Asp Thr Gln Asp
145                 150                 155                 160

Asp Asp Val Glu Glu Ile Gly Asp Gln Asp Asp Ser Pro Ser Asp Asp
                165                 170                 175

Thr Val Glu Gly Thr Pro Pro Ser Gln Glu Asp Gly Lys Ser Pro Thr
            180                 185                 190

Thr Thr Leu Arg Val Gln Glu Ala Ile Leu Lys Glu Leu Gly Ser Glu
        195                 200                 205

Glu Val Arg Lys Val Asn Cys Tyr Gly Gln Glu Val Glu Ser Met Glu
    210                 215                 220

Thr Pro Glu Ser Lys Asp Leu Gly Ser Gln Thr Pro Gln Ala Leu Thr
225                 230                 235                 240

Phe Asn Asp Gly Met Ser Glu Val Lys Asp Glu Gln Thr Pro Gly Trp
                245                 250                 255

Thr Thr Ala Ala Ser Asp Met Lys Phe Glu Tyr Leu Leu Tyr Gly His
            260                 265                 270

His Arg Glu Gln Ile Ala Cys Gln Ala Cys Gly Lys Thr Phe Ser Asp
        275                 280                 285

Glu Gly Arg Leu Arg Lys His Glu Lys Leu His Thr Ala Asp Arg Pro
    290                 295                 300

Phe Val Cys Glu Met Cys Thr Lys Gly Phe Thr Thr Gln Ala His Leu
305                 310                 315                 320

Lys Glu His Leu Lys Ile His Thr Gly Tyr Lys Pro Tyr Ser Cys Glu
                325                 330                 335

Val Cys Gly Lys Ser Phe Ile Arg Ala Pro Asp Leu Lys Lys His Glu
            340                 345                 350
```

-continued

```
Arg Val His Ser Asn Glu Arg Pro Phe Ala Cys His Met Cys Asp Lys
             355                 360                 365
Ala Phe Lys His Lys Ser His Leu Lys Asp His Glu Arg Arg His Arg
        370                 375                 380
Gly Glu Lys Pro Phe Val Cys Gly Ser Cys Thr Lys Ala Phe Ala Lys
385                 390                 395                 400
Ala Ser Asp Leu Lys Arg His Glu Asn Asn Met His Ser Glu Arg Lys
                405                 410                 415
Gln Val Thr Pro Ser Ala Ile Gln Ser Glu Thr Glu Gln Leu Gln Ala
            420                 425                 430
Ala Ala Met Ala Ala Glu Ala Glu Gln Gln Leu Glu Thr Ile Ala Cys
        435                 440                 445
Ser
```

<210> SEQ ID NO 3
<211> LENGTH: 2861
<212> TYPE: DNA
<213> ORGANISM: human

<400> SEQUENCE: 3

```
gattgggtag tccccacctt ttgagcaagt tcagcctggt taagtccaag ctgaattccg      60
gctgcattct tcgctgtcca ggcctgccgg ctctggtgtc tgctggctcc tccttgctcg     120
cctgctccct cctgcttgcc tgagtcaccg ccgccgccgc cgccacagcc atggccgaga     180
gtggtgaaag cggcggtcct ccgggctccc aggatagcgc cgccggagcc gaaggtgctg     240
gcgcccccgc ggccgctgcc tccgcggagc ccaaaatcat gaaagtcacc gcgaagaccc     300
cgaaagaaaa ggaggaattc gccgtgcccg agaatagctc cgtccagcag tctaaggaag     360
aaatctctaa acgttttaaa tcacacactg accaacttgt gttgatattt gctggaaaaa     420
ttttgaaaga tcaagatacc tcgagtcagc atggaattca tgatggactt actgttcacc     480
ttgtcattaa aacacaaaac aggcctcagg atcattcagc tcagcaaaca aatacagctg     540
gaagcaatgt tactacatca tcaactccta atagtaactc tacatctggt tctgctacta     600
gcaacccttt tggtttaggt ggccttgggg gacttgcagg tctgagtagc ttgggtttga     660
atactaccaa cttctctgaa ctacagagtc agatgcagcg acaacttttg tctaaccctg     720
aaatgatggt ccagatcatg gaaaatcct ttgttcagag catgctctca aatcctgacc     780
tgatgagaca gttaattatg gccaatccac aaatgcagca gttgatacag agaaatccag     840
agattagtca tatgttgaat aatccagata taatgagaca aacgttggaa cttgccagga     900
atccagcaat gatgcaggag atgatgagga accaggaccg agctttgagc aacctagaaa     960
gcatcccagg gggatataat gctttaaggc gcatgtacac agatattcag gaaccaatgc    1020
tgagtgctgc acaagagcag tttggtggta atccattgc ttccttggtg agcaatacat    1080
cctctggtga aggtagtcaa ccttcccgta cagaaaatag agatccacta cccaatccat    1140
gggctccaca gacttcccag agttcatcag cttccagcgg cactgccagc actgtgggtg    1200
gcactactgg tagtactgcc agtggcactt ctgggcagag tactactgcg ccaaatttgg    1260
tgcctggagt aggagctagt atgttcaaca caccaggaat gcagagcttg ttgcaacaaa    1320
taactgaaaa cccacaactt atgcaaaaca tgttgtctgc ccctacatg agaagcatga    1380
tgcagtcact aagccagaat cctgaccttg ctgcacagat gatgctgaat aatcccctat    1440
ttgctggaaa tcctcagctt caagaacaaa tgagacaaca gctcccaact ttcctccaac    1500
aaatgcagaa tcctgataca ctatcagcaa tgtcaaaccc tagagcaatg caggcctgt    1560
```

-continued

```
tacagattca gcagggttta cagacattag caacggaagc cccgggcctc atcccagggt   1620
ttactcctgg cttgggggca ttaggaagca ctggaggctc ttcgggaact aatggatcta   1680
acgccacacc tagtgaaaac acaagtccca cagcaggaac cactgaacct ggacatcagc   1740
agtttattca gcagatgctt caggctcttg ctggagtata ttctcagcta cagaatccag   1800
aagtcagatt tcagcaacaa ctggaacaac tcagtgcaat gggattcttg aaccgtgaag   1860
caaacttgca agctctaata gcaacaggag gtgatatcaa tgcagctatt gaaaggttac   1920
tgggctccca gccatcatag cagcatttct gtatcttgaa aaaatgtaat ttattttga   1980 taaccgctct taaatcttta aaataacctg ctttatttca ttttgactct tggaattctg   2040
tgctgttata aacaaaccca atatgatgca ttttaaggtg gagtacagta agatgtgtgg   2100 gttttttctgt attttttcttt tctggaacag tgggaattaa ggctactgca tgcatcactt   2160
ctgcatttat tgtaattttt taaaaacatc acctttata gttgggtgac cagattttgt   2220
cctgcatctg tccagtttat ttgcttttta aacattagcc tatggtagta atttatgtag   2280
aataaaagca ttaaaagaa gcaaatcatt tgcactctat aatttgtggt acagtattgc   2340
ttattgtgac tttggcatgc atttttgcaa acaatgctgt aagatttata ctactgataa   2400
ttttgtttta tttgtataca atatagagta tgcacatttg ggactgcatt tctggaaaca   2460
tactgcaata ggctctctga gcaaaacacc tgtaactaaa aaagtgaaga taagaaaata   2520
ctcttaaagc tgagtatttc ctaattgtat agaatcttac agcatctttg acaaacatct   2580
cccagcaaaa gtgccggtta gtcaggtttg ttgaaaatac agtagaaaag ctgattctgg   2640
ttatctcttt aaggacaatt aattgtacag acacataatg taacattgtc tcaacattca   2700
ttcacagatt gactgtaaat taccttaatc tttgtgcaga ctgaaggaac actgtagtat   2760
accccaaagt gcatttgcct aggacttctc agcttctccc ataggtagtt taacaggcat   2820
taaaatttgt aattgaaatg ctaaaaaaaa aaaaaaaaa a                        2861
```

<210> SEQ ID NO 4
<211> LENGTH: 589
<212> TYPE: PRT
<213> ORGANISM: human

<400> SEQUENCE: 4

```
Met Ala Glu Ser Gly Glu Ser Gly Gly Pro Gly Ser Gln Asp Ser
1               5                   10                  15

Ala Ala Gly Ala Glu Gly Ala Gly Ala Pro Ala Ala Ala Ser Ala
                20                  25                  30

Glu Pro Lys Ile Met Lys Val Thr Ala Lys Thr Pro Lys Glu Lys Glu
                35                  40                  45

Glu Phe Ala Val Pro Glu Asn Ser Ser Val Gln Gln Ser Lys Glu Glu
            50                  55                  60

Ile Ser Lys Arg Phe Lys Ser His Thr Asp Gln Leu Val Leu Ile Phe
65                  70                  75                  80

Ala Gly Lys Ile Leu Lys Asp Gln Asp Thr Ser Ser Gln His Gly Ile
                85                  90                  95

His Asp Gly Leu Thr Val His Leu Val Ile Lys Thr Gln Asn Arg Pro
                100                 105                 110

Gln Asp His Ser Ala Gln Gln Thr Asn Thr Ala Gly Ser Asn Val Thr
            115                 120                 125

Thr Ser Ser Thr Pro Asn Ser Asn Ser Thr Ser Gly Ser Ala Thr Ser
        130                 135                 140
```

-continued

```
Asn Pro Phe Gly Leu Gly Gly Leu Gly Gly Leu Ala Gly Leu Ser Ser
145                 150                 155                 160

Leu Gly Leu Asn Thr Thr Asn Phe Ser Glu Leu Gln Ser Gln Met Gln
                165                 170                 175

Arg Gln Leu Leu Ser Asn Pro Glu Met Met Val Gln Ile Met Glu Asn
                180                 185                 190

Pro Phe Val Gln Ser Met Leu Ser Asn Pro Asp Leu Met Arg Gln Leu
            195                 200                 205

Ile Met Ala Asn Pro Gln Met Gln Gln Leu Ile Gln Arg Asn Pro Glu
        210                 215                 220

Ile Ser His Met Leu Asn Asn Pro Asp Ile Met Arg Gln Thr Leu Glu
225                 230                 235                 240

Leu Ala Arg Asn Pro Ala Met Met Gln Glu Met Met Arg Asn Gln Asp
                245                 250                 255

Arg Ala Leu Ser Asn Leu Glu Ser Ile Pro Gly Gly Tyr Asn Ala Leu
                260                 265                 270

Arg Arg Met Tyr Thr Asp Ile Gln Glu Pro Met Leu Ser Ala Ala Gln
            275                 280                 285

Glu Gln Phe Gly Gly Asn Pro Phe Ala Ser Leu Val Ser Asn Thr Ser
        290                 295                 300

Ser Gly Glu Gly Ser Gln Pro Ser Arg Thr Glu Asn Arg Asp Pro Leu
305                 310                 315                 320

Pro Asn Pro Trp Ala Pro Gln Thr Ser Gln Ser Ser Ala Ser Ser
                325                 330                 335

Gly Thr Ala Ser Thr Val Gly Gly Thr Thr Gly Ser Thr Ala Ser Gly
                340                 345                 350

Thr Ser Gly Gln Ser Thr Thr Ala Pro Asn Leu Val Pro Gly Val Gly
                355                 360                 365

Ala Ser Met Phe Asn Thr Pro Gly Met Gln Ser Leu Leu Gln Gln Ile
370                 375                 380

Thr Glu Asn Pro Gln Leu Met Gln Asn Met Leu Ser Ala Pro Tyr Met
385                 390                 395                 400

Arg Ser Met Met Gln Ser Leu Ser Gln Asn Pro Asp Leu Ala Ala Gln
                405                 410                 415

Met Met Leu Asn Asn Pro Leu Phe Ala Gly Asn Pro Gln Leu Gln Glu
                420                 425                 430

Gln Met Arg Gln Gln Leu Pro Thr Phe Leu Gln Gln Met Gln Asn Pro
            435                 440                 445

Asp Thr Leu Ser Ala Met Ser Asn Pro Arg Ala Met Gln Ala Leu Leu
    450                 455                 460

Gln Ile Gln Gln Gly Leu Gln Thr Leu Ala Thr Glu Ala Pro Gly Leu
465                 470                 475                 480

Ile Pro Gly Phe Thr Pro Gly Leu Gly Ala Leu Gly Ser Thr Gly Gly
                485                 490                 495

Ser Ser Gly Thr Asn Gly Ser Asn Ala Thr Pro Ser Glu Asn Thr Ser
                500                 505                 510

Pro Thr Ala Gly Thr Thr Glu Pro Gly His Gln Gln Phe Ile Gln Gln
            515                 520                 525

Met Leu Gln Ala Leu Ala Gly Val Tyr Ser Gln Leu Gln Asn Pro Glu
530                 535                 540

Val Arg Phe Gln Gln Gln Leu Glu Gln Leu Ser Ala Met Gly Phe Leu
545                 550                 555                 560
```

Asn Arg Glu Ala Asn Leu Gln Ala Leu Ile Ala Thr Gly Gly Asp Ile
            565                 570                 575

Asn Ala Ala Ile Glu Arg Leu Leu Gly Ser Gln Pro Ser
            580                 585

<210> SEQ ID NO 5
<211> LENGTH: 1681
<212> TYPE: DNA
<213> ORGANISM: human

<400> SEQUENCE: 5

| | | | | | |
|---|---|---|---|---|---|
| caccacacct | aggtcggagc | actgtcgtcc | ttcagggctc | cagcctcttg | atattttgt | 60 |
| acttcagtat | cagctcgata | gagcaaaaga | gagagaggac | gagagagggg | gtcagagaag | 120 |
| gggaagcaac | ggctctcacg | ttgggacaat | attatctgga | agctgaagaa | gaaactgaat | 180 |
| actccttcct | tcctccccac | ccattccttt | aaatccggag | ggggaaaaaa | tcccaaggtc | 240 |
| tgcaaaggcg | cggcgctcgg | actataaaac | acaacaaatc | ataaacccgg | cggagcagca | 300 |
| gcggccgcgc | gcgcctcccc | tcccaatgag | ttcctatttc | gtgaactcca | ccttccccgt | 360 |
| cactctggcc | agcgggcagg | agtccttcct | gggccagcta | ccgctctatt | cgtcgggcta | 420 |
| tgcggacccg | ctgagacatt | accccgcgcc | ctacgggcca | gggccgggcc | aggacaaggg | 480 |
| cttttgccact | tcctcctatt | acccgccggc | gggcggtggc | tacggccgag | cggcgccctg | 540 |
| cgactacggg | ccggcgccgg | ccttctaccg | cgagaaagag | tcggcctgcg | cactctccgg | 600 |
| cgccgacgag | cagcccccgt | tccaccccga | gccgcggaag | tcggactgcg | cgcaggacaa | 660 |
| gagcgtgttc | ggcgagacag | aagagcagaa | gtgctccact | ccggtctacc | cgtggatgca | 720 |
| gcggatgaat | tcgtgcaaca | gttcctcctt | tgggcccagc | ggccggcgag | gccgccagac | 780 |
| atacacacgt | taccagacgc | tggagctgga | gaaggagttt | cactacaatc | gctacctgac | 840 |
| gcggcggcgg | cgcatcgaga | tcgcgcacgc | cctgtgcctg | acggagaggc | agatcaagat | 900 |
| atggttccag | aaccgacgca | tgaagtggaa | aaaggagagc | aaactgctca | gcgcgtctca | 960 |
| gctcagtgcc | gaggaggagg | aagaaaaaca | ggccgagtga | aggtgctgga | aagggaggga | 1020 |
| ggacgcgagg | ggaaaggcct | gtggggagcc | acgggcgtca | gagagacccg | ggaaggaagg | 1080 |
| ctctcgggtg | ggggagccag | gagacctgct | ctccggcgca | gacaggcggg | gcccagcgct | 1140 |
| ctcctggacg | cccccgcccg | cacagctccc | ggcgggtgct | ctgaggcctc | actactcgag | 1200 |
| cccacccagc | atcccgcgcg | cccttccttc | ccgaggaact | cgcctcagcc | tgatcaggct | 1260 |
| tcctggtgag | aactgaggag | cggactcact | tgatgtttcc | tggaagcaga | gcaaaatgct | 1320 |
| cttgtccctg | tcgcgtctca | ttttgtccat | gtccccgtg | cacggttcaa | tggtagattc | 1380 |
| gctgtcccct | cagcgggggc | cttgaagact | ccctgatccc | agacctgtcg | tctctcccac | 1440 |
| cccctcccca | aagccactgg | aaggagcaca | tactacctag | aagtaagaag | aggagcctca | 1500 |
| gaagaaaaca | aagttctatt | ttattaattt | tctatgtgtt | gtgtttgtag | tcttgtctta | 1560 |
| gctctggacg | tgaaatactt | cgatgatgat | gatgatgatg | atgatgatga | taataataat | 1620 |
| aataataaca | acaacaacaa | caataataaa | gatgtgaaaa | ctcaaaaaaa | aaaaaaaaa | 1680 |
| a | | | | | | 1681 |

<210> SEQ ID NO 6
<211> LENGTH: 224
<212> TYPE: PRT
<213> ORGANISM: human

```
<400> SEQUENCE: 6

Met Ser Ser Tyr Phe Val Asn Ser Thr Phe Pro Val Thr Leu Ala Ser
1               5                   10                  15

Gly Gln Glu Ser Phe Leu Gly Gln Leu Pro Leu Tyr Ser Ser Gly Tyr
            20                  25                  30

Ala Asp Pro Leu Arg His Tyr Pro Ala Pro Tyr Gly Pro Gly Pro Gly
        35                  40                  45

Gln Asp Lys Gly Phe Ala Thr Ser Ser Tyr Tyr Pro Pro Ala Gly Gly
    50                  55                  60

Gly Tyr Gly Arg Ala Ala Pro Cys Asp Tyr Gly Pro Ala Pro Ala Phe
65              70                  75                  80

Tyr Arg Glu Lys Glu Ser Ala Cys Ala Leu Ser Gly Ala Asp Glu Gln
                85                  90                  95

Pro Pro Phe His Pro Glu Pro Arg Lys Ser Asp Cys Ala Gln Asp Lys
            100                 105                 110

Ser Val Phe Gly Glu Thr Glu Gln Lys Cys Ser Thr Pro Val Tyr
            115                 120                 125

Pro Trp Met Gln Arg Met Asn Ser Cys Asn Ser Ser Phe Gly Pro
130                 135                 140

Ser Gly Arg Arg Gly Arg Gln Thr Tyr Thr Arg Tyr Gln Thr Leu Glu
145                 150                 155                 160

Leu Glu Lys Glu Phe His Tyr Asn Arg Tyr Leu Thr Arg Arg Arg Arg
                165                 170                 175

Ile Glu Ile Ala His Ala Leu Cys Leu Thr Glu Arg Gln Ile Lys Ile
            180                 185                 190

Trp Phe Gln Asn Arg Arg Met Lys Trp Lys Lys Glu Ser Lys Leu Leu
            195                 200                 205

Ser Ala Ser Gln Leu Ser Ala Glu Glu Glu Glu Lys Gln Ala Glu
210                 215                 220

<210> SEQ ID NO 7
<211> LENGTH: 729
<212> TYPE: DNA
<213> ORGANISM: human

<400> SEQUENCE: 7
ggcaggagct acccttcccg tggccccgga ccttgggtgg gctgtgggct cagggagcgg   60
aggggaggcc ttaagcatcc actctctgcc cggtgttttt gttctcatca gggagcctca  120
gatgggaagg gactcgagcc ccacctgtcc ctggactctg aatgccacg gaattaaccc  180 gagcaggcat ggaggcctct gctctcacct catcagcagt gaccagtgtg gccaaagtgg  240
tcagggtggc ctctggctct gccgtagttt tgcccctggc caggattgct acagttgtga  300
ttggaggagt tgtggctgtg cccatggtgc tcagtgccat gggcttcact gcggcgggaa  360
tcgcctcgtc ctccatagca gccaagatga tgtccgcggc ggccattgcc aatggggtg   420 gagttgcctc gggcagcctt gtggctactc tgcagtcact gggagcaact ggactctccg  480
gattgaccaa gttcatcctg gctccattg gtctgccat tgcggctgtc attgcgaggt   540
tctactagct ccctgcccct cgccctgcag agaagagaac catgccaggg gagaaggcac  600
ccagccatcc tgacccagcg aggagccaac tatcccaaat atacctgggg tgaaatatac  660
caaattctgc atctccagag gaaaataaga ataaagatg aattgttgca actcaaaaaa  720
aaaaaaaaa                                                          729
```

-continued

<210> SEQ ID NO 8
<211> LENGTH: 119
<212> TYPE: PRT
<213> ORGANISM: human

<400> SEQUENCE: 8

Met Glu Ala Ser Ala Leu Thr Ser Ser Ala Val Thr Ser Val Ala Lys
1               5                   10                  15

Val Val Arg Val Ala Ser Gly Ser Ala Val Val Leu Pro Leu Ala Arg
            20                  25                  30

Ile Ala Thr Val Val Ile Gly Gly Val Val Ala Val Pro Met Val Leu
        35                  40                  45

Ser Ala Met Gly Phe Thr Ala Ala Gly Ile Ala Ser Ser Ile Ala
    50                  55                  60

Ala Lys Met Met Ser Ala Ala Ile Ala Asn Gly Gly Gly Val Ala
65                  70                  75                  80

Ser Gly Ser Leu Val Ala Thr Leu Gln Ser Leu Gly Ala Thr Gly Leu
                85                  90                  95

Ser Gly Leu Thr Lys Phe Ile Leu Gly Ser Ile Gly Ser Ala Ile Ala
            100                 105                 110

Ala Val Ile Ala Arg Phe Tyr
        115

<210> SEQ ID NO 9
<211> LENGTH: 1458
<212> TYPE: DNA
<213> ORGANISM: human

<400> SEQUENCE: 9
gccgccgccg gcctagttac catcacaccc cgggaggagc cgcagctgcc gcagccggcc      60
ccagtcacca tcaccgcaac catgagcagc gaggccgaga cccagcagcc gcccgccgcc     120
ccccccgccg cccccgccct cagcgccgcc gacactaagc ccggcactac gggcagcggc     180
gcagggagcg gtggcccggg cggcctcaca tcggcggcgc ctgccggcgg ggacaagaag     240
gtcatcgcaa cgaaggtttt gggaacagta aatggttca atgtaaggaa cggatatggt      300
ttcatcaaca ggaatgacac caaggaagat gtatttgtac accagactgc cataaagaag     360
aataacccca ggaagtaccct tcgcagtgta ggagatggag agactgtgga gtttgatgtt     420
gttgaaggag aaaagggtgc ggaggcagca atgttacag gtcctggtgg tgttccagtt     480
caaggcagta aatatgcagc agaccgtaac cattatagac gctatccacg tcgtagggt      540
cctccacgca attaccagca aaattaccag aatagtgaga gtggggaaaa gaacgaggga     600
tcggagagtg ctcccgaagg ccaggcccaa caacgccggc cctaccgcag gcgaaggttc     660
ccaccttact acatgcggag accctatggg cgtcgaccac agtattccaa ccctcctgtg     720
cagggagaag tgatggaggg tgctgacaac caggtgcag gagaacaagg tagaccagtg     780
aggcagaata tgtatcgggg atatagacca cgattccgca ggggccctcc tcgccaaaga     840
cagcctagag aggacggcaa tgaagaagat aaagaaaatc aaggagatga gacccaaggt     900
cagcagccac ctcaacgtcg gtaccgccgc aacttcaatt accgacgcag acgcccagaa     960
aaccctaaac acaagatgg caaagagaca aaagcagccg atccaccagc tgagaattcg    1020
tccgctcccg aggctgagca gggcggggct gagtaaatgc cggcttacca tctctaccat    1080
catccggttt agtcatccaa caagaagaaa tatgaaattc cagcaataag aaatgaacaa    1140
aagattggag ctgaagacct aaagtgcttg cttttgccc gttgaccaga taaatagaac    1200

-continued

```
tatctgcatt atctatgcag catggggttt ttattatttt tacctaaaga cgtctctttt    1260
tggtaataac aaacgtgttt tttaaaaaag cctggttttt ctcaatacgc ctttaaaggt    1320
ttttaaattg tttcatatct ggtcaagttg agattttaa gaacttcatt tttaatttgt    1380
aataaaagtt tacaacttga ttttttcaaa aaagtcaaca aactgcaagc acctgttaat    1440
aaataattgt ctttgtgt                                                  1458
```

<210> SEQ ID NO 10
<211> LENGTH: 324
<212> TYPE: PRT
<213> ORGANISM: human

<400> SEQUENCE: 10

```
Met Ser Ser Glu Ala Glu Thr Gln Gln Pro Ala Ala Pro Pro Ala
  1               5                  10                  15

Ala Pro Ala Leu Ser Ala Ala Asp Thr Lys Pro Gly Thr Thr Gly Ser
                 20                  25                  30

Gly Ala Gly Ser Gly Gly Pro Gly Gly Leu Thr Ser Ala Ala Pro Ala
                 35                  40                  45

Gly Gly Asp Lys Lys Val Ile Ala Thr Lys Val Leu Gly Thr Val Lys
 50                  55                  60

Trp Phe Asn Val Arg Asn Gly Tyr Gly Phe Ile Asn Arg Asn Asp Thr
 65                  70                  75                  80

Lys Glu Asp Val Phe Val His Gln Thr Ala Ile Lys Lys Asn Asn Pro
                 85                  90                  95

Arg Lys Tyr Leu Arg Ser Val Gly Asp Gly Glu Thr Val Glu Phe Asp
                100                 105                 110

Val Val Glu Gly Glu Lys Gly Ala Glu Ala Ala Asn Val Thr Gly Pro
                115                 120                 125

Gly Gly Val Pro Val Gln Gly Ser Lys Tyr Ala Ala Asp Arg Asn His
                130                 135                 140

Tyr Arg Arg Tyr Pro Arg Arg Arg Gly Pro Pro Arg Asn Tyr Gln Gln
145                 150                 155                 160

Asn Tyr Gln Asn Ser Glu Ser Gly Glu Lys Asn Glu Gly Ser Glu Ser
                165                 170                 175

Ala Pro Glu Gly Gln Ala Gln Gln Arg Arg Pro Tyr Arg Arg Arg
                180                 185                 190

Phe Pro Pro Tyr Tyr Met Arg Arg Pro Tyr Gly Arg Arg Pro Gln Tyr
                195                 200                 205

Ser Asn Pro Pro Val Gln Gly Glu Val Met Glu Gly Ala Asp Asn Gln
                210                 215                 220

Gly Ala Gly Glu Gln Gly Arg Pro Val Arg Gln Asn Met Tyr Arg Gly
225                 230                 235                 240

Tyr Arg Pro Arg Phe Arg Arg Gly Pro Pro Arg Gln Arg Gln Pro Arg
                245                 250                 255

Glu Asp Gly Asn Glu Glu Asp Lys Glu Asn Gln Gly Asp Glu Thr Gln
                260                 265                 270

Gly Gln Gln Pro Pro Gln Arg Arg Tyr Arg Arg Asn Phe Asn Tyr Arg
                275                 280                 285

Arg Arg Arg Pro Glu Asn Pro Lys Pro Gln Asp Gly Lys Glu Thr Lys
                290                 295                 300

Ala Ala Asp Pro Pro Ala Glu Asn Ser Ser Ala Pro Glu Ala Glu Gln
305                 310                 315                 320

Gly Gly Ala Glu
```

-continued

<210> SEQ ID NO 11
<211> LENGTH: 4197
<212> TYPE: DNA
<213> ORGANISM: human

<400> SEQUENCE: 11

| | | | | | |
|---|---|---|---|---|---|
| gcggaggccg | ttcctggctt | tgtagctcgc | tcaagatggc | ggcgcagcca | ccccgcggga | 60 |
| tacgcctcag | cgcgctttgc | ccgaagtttt | tacatacaaa | ttctactagt | cacacctggc | 120 |
| cattcagtgc | agttgctgaa | ttaatagata | atgcttatga | tcctgatgtg | aacgctaaac | 180 |
| aaatatggat | tgacaaaaca | gtgataaatg | accatatatg | cttgacattc | accgacaatg | 240 |
| ggaatggtat | gacttctgat | aaattacata | aaatgctaag | ctttggcttc | agtgacaaac | 300 |
| tcaccatgaa | tggtcatgtc | ccagttggat | tatatgggaa | tggcttcaag | tcgggttcta | 360 |
| tgcgtctggg | taaagacgca | atcgttttta | ccaaaaatgg | agaaagcatg | agcgtgggcc | 420 |
| ttttgtctca | gacctacttg | gaagtcataa | agcggagca | tgttgttgtt | ccaatagtgg | 480 |
| cattcaacaa | gcaccgacag | atgattaatt | tagcagaatc | aaaagccagc | cttgctgcaa | 540 |
| ttctggaaca | ttctctgttt | tccacggaac | agaagttact | ggcagaactt | gatgctatta | 600 |
| taggcaagaa | ggggacgagg | atcatcattt | ggaatcttag | aagctacaaa | aatgcaacag | 660 |
| agttcgattt | tgaaaaggat | aaatatgata | tcagaattcc | cgaggattta | tgatgagataa | 720 |
| cagggaagaa | ggggtacaag | aagcaggaaa | ggatggacca | gattgcccct | gagagtgact | 780 |
| attccctgag | ggcttattgc | agtatattat | atctaaagcc | aagaatgcag | atcatcctac | 840 |
| gtggacagaa | agtgaagaca | cagctggttt | cgaagagtct | tgcctacatc | gaacgtgatg | 900 |
| tttatcgacc | aaaattttta | tctaaaacag | tgagaattac | ctttggattc | aactgcagaa | 960 |
| ataaagatca | ttatgggata | atgatgtatc | acagaaatag | actcatcaaa | gcttatgaaa | 1020 |
| aagttggatg | tcagttaagg | gcaaacaaca | tgggtgttgg | agtggttgga | attatagagt | 1080 |
| gtaatttcct | taagccaact | cataataaac | aagatttcga | ctatactaat | gagtacagac | 1140 |
| ttacaataac | agcactagga | gaaaagctga | atgattactg | gaatgaaatg | aaagtgaaga | 1200 |
| aaaatacaga | atatcctcta | aatttgccag | ttgaagatat | acagaagcgt | cctgatcaga | 1260 |
| catgggttca | gtgtgatgcc | tgtctaaagt | ggcggaaatt | acctgatggg | atggatcaac | 1320 |
| ttcctgaaaa | atggtattgc | tccaataacc | ctgacccaca | gttcagaaat | tgtgaggttc | 1380 |
| cagaagaacc | tgaagatgag | gatttggtac | atcccactta | tgaaaaaacc | tacaaaaaga | 1440 |
| ccaacaagga | aaaattcagg | atcagacaac | cggaaatgat | ccctcggatt | aatgctgaac | 1500 |
| tgttgtttcg | gccaactgct | ctttcaactc | caagcttttc | ttctcctaag | gaaagtgttc | 1560 |
| caagaagaca | tctttcagaa | ggaacaaatt | cttatgcgac | aagacttcta | ataatcatc | 1620 |
| aagttccacc | tcagtctgaa | cctgagagca | acagcttgaa | acggagactt | tctactcgtt | 1680 |
| cctcaatttt | gaatgcaaag | aatcggagat | tgagtagtca | gtttgaaaat | tcagtttata | 1740 |
| aaggtgatga | tgatgatgaa | gatgtcatca | tcttagaaga | aaacagtacc | cccaaacctg | 1800 |
| cagtagatca | tgatattgac | atgaaatcag | aacagagtca | cgttgagcaa | ggtggtgttc | 1860 |
| aggttgagtt | tgtgggtgac | agtgaacctt | gtggccagac | tggttcaaca | agcacctcat | 1920 |
| catcccgatg | cgaccaggga | aatactgcag | ctacccagac | tgaagtacca | agtttagttg | 1980 |
| ttaaaaaaga | agaaactgtt | gaagacgaga | tagacgtaag | aaatgatgca | gtgattctgc | 2040 |
| cctcctgtgt | agaagctgaa | gcaaagatac | atgaaaccca | ggaaccacc | gataaatctg | 2100 |

-continued

```
cagatgatgc aggctgccaa ttacaagaac tgagaaacca gctactcctt gtcactgagg    2160
aaaaagagaa ttataaaaga cagtgtcata tgtttactga tcaaatcaaa gtgttacaac    2220
agaggatact agaaatgaat gacaagtatg ttaagaaaga aacttgccat cagtccactg    2280
aaaccgatgc tgtattttta cttgaaagta ttaatggcaa atctgaaagt ccagaccata    2340
tggtatctca gtatcagcaa gctttggaag aaatagaaag gctgaaaaaa caatgtagtg    2400
ctttgcaaca tgtaaaggct gaatgcagcc agtgttccaa taatgagagt aaaagtgaaa    2460
tggatgagat ggctgtgcag cttgacgatg tgtttagaca actggacaaa tgcagtattg    2520
agagggacca gtataaaagt gaggttgaat tgctggaaat ggaaaagtca caaatccgtt    2580
cacagtgtga agaactcaaa actgaagtag aacagttaaa atctacaaat caacagacgg    2640
caacagatgt ttcaacatca agtaacattg aggagtctgt aaatcatatg gatggagaaa    2700
gcctcaaact ccgatctctt cgagttaacg taggacaact gctggctatg attgtgcctg    2760
atcttgatct tcagcaagtg aattacgatg ttgatgtagt tgatgagatt ttaggacaag    2820
ttgttgaaca aatgagtgaa atcagtagta cttaaagtat atgttatgta agataaaata    2880
tttgctcaat tcttttggtt gtacagcttt caaaatataa ttaattttgt tttatagata    2940
tgataggcaa cagactgaaa accataatct ttactgtatt ctatgcattc aaatgtggtc    3000
acaaatattg tggacacatt atcttatgtt ttgaaatacc tgtgaattgt tggcattgag    3060
cagctgaagc taactcatga ctctgttttg aatgtaaata tttgtaatta agcctgcaca    3120 tatttttta ttgccctaga gtactcaagt gttttcacc aagagctttt caggttgccc    3180
ctaagctttg tgcaattttt tctggttccc caaagtgtat ttttctctaa gtcgagggct    3240
atgccataat acaaatggaa atgttacctt tgattttctt ataaaggagt ttaaatagga    3300
tttttaaata atgtagtaac actcctgata caactctggt tataagtgaa ttgagcatta    3360
atgtttcttt tgtataaatt cctgtcctga atatttat tcatgaaaat aaggtaagca    3420
aaaaccaact ccatttgcc aggattttgt tgtgctgaga ttgccaatca cggttaaaca    3480
caaagtgttt ttatagaatg aagaaacagt ctttaacaga aaaaaggtat tgaaatatta    3540
aatggccacc aagtttactt tgaagcccat ttttggctgt ttagtcagca tgaagtgggc    3600
atgataattt tttaatattt cttttttgtga aatttcctgt acagccttt gtaggattac    3660 tacaggttaa tgtgagttga ggaagacagt ctttctcaaa caatactaca tacctttaat    3720
tatattacaa acctaagtgt tttatatcct agagtcaagg aacaaatttc cttaggatta    3780
tagtattaca tgccataaaa tactatgctt tattggtccc atgttttgtg caattttaaa    3840
gagatggctt tctattaagt ataaactatg tatatataag aaccatattt tccacaacta    3900
aaatgtgcat tattttttcc aaagttttat cattgctatt tattttacc tttgttttg     3960 aacattcaat ccgttcattt tgtatgtatg cttaatacgt gtcggtcata tacagtattg    4020 aattttact gtatagtaat tctggaaaga gcaaataaat gaagattgtt tttatttgcc    4080
tgataaagta attgaaagtg tattttggt atgaagctgg ttttctgtca caattgtaat    4140
ttcccaaatt ttaaaatatc ttataataaa ataaaaatat atgatggcta actgttc      4197
```

<210> SEQ ID NO 12
<211> LENGTH: 939
<212> TYPE: PRT
<213> ORGANISM: human

<400> SEQUENCE: 12

```
Met Ala Ala Gln Pro Pro Arg Gly Ile Arg Leu Ser Ala Leu Cys Pro
1               5                   10                  15

Lys Phe Leu His Thr Asn Ser Thr Ser His Thr Trp Pro Phe Ser Ala
            20                  25                  30

Val Ala Glu Leu Ile Asp Asn Ala Tyr Asp Pro Asp Val Asn Ala Lys
        35                  40                  45

Gln Ile Trp Ile Asp Lys Thr Val Ile Asn Asp His Ile Cys Leu Thr
    50                  55                  60

Phe Thr Asp Asn Gly Asn Gly Met Thr Ser Asp Lys Leu His Lys Met
65                  70                  75                  80

Leu Ser Phe Gly Phe Ser Asp Lys Leu Thr Met Asn Gly His Val Pro
                85                  90                  95

Val Gly Leu Tyr Gly Asn Gly Phe Lys Ser Gly Ser Met Arg Leu Gly
            100                 105                 110

Lys Asp Ala Ile Val Phe Thr Lys Asn Gly Glu Ser Met Ser Val Gly
        115                 120                 125

Leu Leu Ser Gln Thr Tyr Leu Glu Val Ile Lys Ala Glu His Val Val
    130                 135                 140

Val Pro Ile Val Ala Phe Asn Lys His Arg Gln Met Ile Asn Leu Ala
145                 150                 155                 160

Glu Ser Lys Ala Ser Leu Ala Ala Ile Leu Glu His Ser Leu Phe Ser
                165                 170                 175

Thr Glu Gln Lys Leu Leu Ala Glu Leu Asp Ala Ile Ile Gly Lys Lys
            180                 185                 190

Gly Thr Arg Ile Ile Ile Trp Asn Leu Arg Ser Tyr Lys Asn Ala Thr
        195                 200                 205

Glu Phe Asp Phe Glu Lys Asp Lys Tyr Asp Ile Arg Ile Pro Glu Asp
    210                 215                 220

Leu Asp Glu Ile Thr Gly Lys Lys Gly Tyr Lys Lys Gln Glu Arg Met
225                 230                 235                 240

Asp Gln Ile Ala Pro Glu Ser Asp Tyr Ser Leu Arg Ala Tyr Cys Ser
                245                 250                 255

Ile Leu Tyr Leu Lys Pro Arg Met Gln Ile Ile Leu Arg Gly Gln Lys
            260                 265                 270

Val Lys Thr Gln Leu Val Ser Lys Ser Leu Ala Tyr Ile Glu Arg Asp
        275                 280                 285

Val Tyr Arg Pro Lys Phe Leu Ser Lys Thr Val Arg Ile Thr Phe Gly
    290                 295                 300

Phe Asn Cys Arg Asn Lys Asp His Tyr Gly Ile Met Met Tyr His Arg
305                 310                 315                 320

Asn Arg Leu Ile Lys Ala Tyr Glu Lys Val Gly Cys Gln Leu Arg Ala
                325                 330                 335

Asn Asn Met Gly Val Gly Val Gly Ile Ile Glu Cys Asn Phe Leu
            340                 345                 350

Lys Pro Thr His Asn Lys Gln Asp Phe Asp Tyr Thr Asn Glu Tyr Arg
        355                 360                 365

Leu Thr Ile Thr Ala Leu Gly Glu Lys Leu Asn Asp Tyr Trp Asn Glu
    370                 375                 380

Met Lys Val Lys Lys Asn Thr Glu Tyr Pro Leu Asn Leu Pro Val Glu
385                 390                 395                 400

Asp Ile Gln Lys Arg Pro Asp Gln Thr Trp Val Gln Cys Asp Ala Cys
                405                 410                 415
```

```
Leu Lys Trp Arg Lys Leu Pro Asp Gly Met Asp Gln Leu Pro Glu Lys
            420                 425                 430

Trp Tyr Cys Ser Asn Asn Pro Asp Pro Gln Phe Arg Asn Cys Glu Val
            435                 440                 445

Pro Glu Glu Pro Glu Asp Glu Asp Leu Val His Pro Thr Tyr Glu Lys
            450                 455                 460

Thr Tyr Lys Lys Thr Asn Lys Glu Lys Phe Arg Ile Arg Gln Pro Glu
465                 470                 475                 480

Met Ile Pro Arg Ile Asn Ala Glu Leu Leu Phe Arg Pro Thr Ala Leu
            485                 490                 495

Ser Thr Pro Ser Phe Ser Pro Lys Glu Ser Val Pro Arg Arg His
            500                 505                 510

Leu Ser Glu Gly Thr Asn Ser Tyr Ala Thr Arg Leu Leu Asn Asn His
            515                 520                 525

Gln Val Pro Pro Gln Ser Glu Pro Glu Ser Asn Ser Leu Lys Arg Arg
            530                 535                 540

Leu Ser Thr Arg Ser Ser Ile Leu Asn Ala Lys Asn Arg Arg Leu Ser
545                 550                 555                 560

Ser Gln Phe Glu Asn Ser Val Tyr Lys Gly Asp Asp Asp Glu Asp
            565                 570                 575

Val Ile Ile Leu Glu Glu Asn Ser Thr Pro Lys Pro Ala Val Asp His
            580                 585                 590

Asp Ile Asp Met Lys Ser Glu Gln Ser His Val Glu Gln Gly Gly Val
            595                 600                 605

Gln Val Glu Phe Val Gly Asp Ser Glu Pro Cys Gly Gln Thr Gly Ser
            610                 615                 620

Thr Ser Thr Ser Ser Ser Arg Cys Asp Gln Gly Asn Thr Ala Ala Thr
625                 630                 635                 640

Gln Thr Glu Val Pro Ser Leu Val Val Lys Lys Glu Thr Val Glu
            645                 650                 655

Asp Glu Ile Asp Val Arg Asn Asp Ala Val Ile Leu Pro Ser Cys Val
            660                 665                 670

Glu Ala Glu Ala Lys Ile His Glu Thr Gln Glu Thr Thr Asp Lys Ser
            675                 680                 685

Ala Asp Asp Ala Gly Cys Gln Leu Gln Glu Leu Arg Asn Gln Leu Leu
            690                 695                 700

Leu Val Thr Glu Glu Lys Glu Asn Tyr Lys Arg Gln Cys His Met Phe
705                 710                 715                 720

Thr Asp Gln Ile Lys Val Leu Gln Gln Arg Ile Leu Glu Met Asn Asp
            725                 730                 735

Lys Tyr Val Lys Lys Glu Thr Cys His Gln Ser Thr Glu Thr Asp Ala
            740                 745                 750

Val Phe Leu Leu Glu Ser Ile Asn Gly Lys Ser Glu Ser Pro Asp His
            755                 760                 765

Met Val Ser Gln Tyr Gln Gln Ala Leu Glu Glu Ile Glu Arg Leu Lys
            770                 775                 780

Lys Gln Cys Ser Ala Leu Gln His Val Lys Ala Glu Cys Ser Gln Cys
785                 790                 795                 800

Ser Asn Asn Glu Ser Lys Ser Glu Met Asp Glu Met Ala Val Gln Leu
            805                 810                 815

Asp Asp Val Phe Arg Gln Leu Asp Lys Cys Ser Ile Glu Arg Asp Gln
            820                 825                 830
```

```
Tyr Lys Ser Glu Val Glu Leu Leu Glu Met Glu Lys Ser Gln Ile Arg
        835                 840                 845

Ser Gln Cys Glu Glu Leu Lys Thr Glu Val Glu Gln Leu Lys Ser Thr
    850                 855                 860

Asn Gln Gln Thr Ala Thr Asp Val Ser Thr Ser Ser Asn Ile Glu Glu
865                 870                 875                 880

Ser Val Asn His Met Asp Gly Glu Ser Leu Lys Leu Arg Ser Leu Arg
                885                 890                 895

Val Asn Val Gly Gln Leu Leu Ala Met Ile Val Pro Asp Leu Asp Leu
            900                 905                 910

Gln Gln Val Asn Tyr Asp Val Asp Val Asp Glu Ile Leu Gly Gln
        915                 920                 925

Val Val Glu Gln Met Ser Glu Ile Ser Ser Thr
    930                 935

<210> SEQ ID NO 13
<211> LENGTH: 2133
<212> TYPE: DNA
<213> ORGANISM: human

<400> SEQUENCE: 13
cgggagagcg cgctctgcct gccgcctgcc tgcctgccac tgagggttcc cagcaccatg      60
agggcctgga tcttctttct cctttgcctg gcgggagggg ccttggcagc ccctcagcaa     120
gaagccctgc ctgatgagac agaggtggtg aagaaactg tggcagaggt gactgaggta     180
tctgtgggag ctaatcctgt ccaggtgaa gtaggagaat tgatgatgg tgcagaggaa     240
accgaagagg aggtggtggc ggaaaatccc tgccagaacc accactgcaa acacggcaag    300
gtgtgcgagc tggatgagaa caacaccccc atgtgcgtgt gccaggaccc caccagctgc    360
ccagccccca ttggcgagtt tgagaaggtg tgcagcaatg acaacaagac cttcgactct    420
tcctgccact tctttgccac aaagtgcacc ctggagggca ccaagaaggg ccacaagctc    480
cacctggact acatcgggcc ttgcaaatac atcccccctt gcctggactc tgagctgacc    540
gaattccccc tgcgcatgcg ggactggctc aagaacgtcc tggtcaccct gtatgagagg    600
gatgaggaca caaaccttct gactgagaag cagaagctgc gggtgaagaa gatccatgag    660
aatgagaagc gcctggaggc aggagaccac ccgtggagc tgctggcccg ggacttcgag    720
aagaactata acatgtacat cttccctgta cactggcagt tcggccagct ggaccagcac    780
cccattgacg gtaccctctc ccacaccgag ctggctccac tgcgtgctcc cctcatcccc    840
atggagcatt gcaccacccg cttttcgag acctgtgacc tggacaatga caagtacatc    900
gccctggatg agtgggccgg ctgcttcggc atcaagcaga aggatatcga caaggatctt    960
gtgatctaaa tccactcctt ccacagtacc ggattctctc tttaaccctc cccttcgtgt   1020
ttccccaat gtttaaaatg tttggatggt tgttgttct gcctggagac aagtgctaa    1080
catagattta agtgaataca ttaacggtgc taaaaatgaa aattctaacc caagacatga   1140
cattcttagc tgtaacttaa ctattaaggc cttttccaca cgcattaata gtcccatttt   1200
tctcttgcca tttgtagctt tgcccattgt cttattggca catgggtgga cacgatctg   1260
ctgggctctg ccttaaacac acattgcagc ttcaactttt ctctttagtg ttctgtttga   1320
aactaatact taccgagtca gactttgtgt tcatttcatt tcagggtctt ggctgcctgt   1380
gggcttcccc aggtggcctg gaggtgggca aagggaagta acagacacac gatgttgtca   1440
aggatggttt tgggactaga ggctcagtgg tgggagagat ccctgcagaa tccaccaacc   1500
```

-continued

```
agaacgtggt tgcctgagg ctgtaactga gagaaagatt ctggggctgt cttatgaaaa    1560
tatagacatt ctcacataag cccagttcat caccatttcc tcctttacct ttcagtgcag    1620
tttcttttca cattaggctg ttggttcaaa cttttgggag cacggactgt cagttctctg    1680
ggaagtggtc agcgcatcct gcagggcttc tcctcctctg tcttttggag aaccagggct    1740
cttctcaggg gctctaggga ctgccaggct gtttcagcca ggaaggccaa aatcaagagt    1800
gagatgtaga aagttgtaaa atagaaaaag tggagttggt gaatcggttg ttctttcctc    1860
acatttggat gattgtcata aggtttttag catgttcctc cttttcttca ccctcccctt    1920
tgttcttcta ttaatcaaga gaaacttcaa agttaatggg atggtcggat ctcacaggct    1980
gagaactcgt tcacctccaa gcatttcatg aaaaagctgc ttcttattaa tcatacaaac    2040
tctcaccatg atgtgaagag tttcacaaat ctttcaaaat aaaagtaat gacttagaaa    2100 ctgaaaaaaa aaaaaaaaaa aaaaaaaaaa aaa                                 2133
```

<210> SEQ ID NO 14
<211> LENGTH: 303
<212> TYPE: PRT
<213> ORGANISM: human

<400> SEQUENCE: 14

```
Met Arg Ala Trp Ile Phe Phe Leu Leu Cys Leu Ala Gly Arg Ala Leu
1               5                   10                  15

Ala Ala Pro Gln Gln Glu Ala Leu Pro Asp Glu Thr Glu Val Val Glu
            20                  25                  30

Glu Thr Val Ala Glu Val Thr Glu Val Ser Val Gly Ala Asn Pro Val
        35                  40                  45

Gln Val Glu Val Gly Phe Asp Asp Gly Ala Glu Glu Thr Glu Glu
    50                  55                  60

Glu Val Val Ala Glu Asn Pro Cys Gln Asn His His Cys Lys His Gly
65                  70                  75                  80

Lys Val Cys Glu Leu Asp Glu Asn Asn Thr Pro Met Cys Val Cys Gln
                85                  90                  95

Asp Pro Thr Ser Cys Pro Ala Pro Ile Gly Glu Phe Glu Lys Val Cys
            100                 105                 110

Ser Asn Asp Asn Lys Thr Phe Asp Ser Ser Cys His Phe Phe Ala Thr
        115                 120                 125

Lys Cys Thr Leu Glu Gly Thr Lys Lys Gly His Lys Leu His Leu Asp
    130                 135                 140

Tyr Ile Gly Pro Cys Lys Tyr Ile Pro Pro Cys Leu Asp Ser Glu Leu
145                 150                 155                 160

Thr Glu Phe Pro Leu Arg Met Arg Asp Trp Leu Lys Asn Val Leu Val
                165                 170                 175

Thr Leu Tyr Glu Arg Asp Glu Asp Asn Asn Leu Leu Thr Glu Lys Gln
            180                 185                 190

Lys Leu Arg Val Lys Lys Ile His Glu Asn Glu Lys Arg Leu Glu Ala
        195                 200                 205

Gly Asp His Pro Val Glu Leu Leu Ala Arg Asp Phe Glu Lys Asn Tyr
    210                 215                 220

Asn Met Tyr Ile Phe Pro Val His Trp Gln Phe Gly Gln Leu Asp Gln
225                 230                 235                 240

His Pro Ile Asp Gly Tyr Leu Ser His Thr Glu Leu Ala Pro Leu Arg
                245                 250                 255
```

Ala Pro Leu Ile Pro Met Glu His Cys Thr Thr Arg Phe Phe Glu Thr
    260                 265                 270

Cys Asp Leu Asp Asn Asp Lys Tyr Ile Ala Leu Asp Glu Trp Ala Gly
            275                 280                 285

Cys Phe Gly Ile Lys Gln Lys Asp Ile Asp Lys Asp Leu Val Ile
    290                 295                 300

<210> SEQ ID NO 15
<211> LENGTH: 1866
<212> TYPE: DNA
<213> ORGANISM: Human

<400> SEQUENCE: 15

| | | | | | |
|---|---|---|---|---|---|
| atggcggcgg | cagcagtcga | cagcgcgatg | gaggtggtgc | cggcgctggc | ggaggaggcc | 60 |
| gcgccggagg | tagcgggcct | cagctgcctc | gtcaacctgc | cgggtgaggt | gctggagtac | 120 |
| atcctgtgct | gcggctcgct | gacggccgcc | gacatcggcc | gtgtctccag | cacctgccgg | 180 |
| cggctgcgcg | agctgtgcca | gagcagcggg | aaggtgtgga | aggagcagtt | ccgggtgagg | 240 |
| tggccttccc | ttatgaaaca | ctacagcccc | accgactacg | tcaattggtt | ggaagagtat | 300 |
| aaagttcggc | aaaaagctgg | gttagaagcg | cggaagattg | tagcctcgtt | ctcaaagagg | 360 |
| ttcttttcag | agcacgttcc | ttgtaatggc | ttcagtgaca | ttgagaacct | tgaaggacca | 420 |
| gagattttt | ttgaggatga | actggtgtgt | atcctaaata | tggaaggaag | aaaagctttg | 480 |
| acctggaaat | actacgcaaa | aaaaattctt | tactacctgc | ggcaacagaa | gatcttaaat | 540 |
| aatcttaagg | cctttcttca | gcagccagat | gactatgagt | cgtatcttga | aggtgctgta | 600 |
| tatattgacc | agtactgcaa | tcctctctcc | gacatcagcc | tcaaagacat | ccaggcccaa | 660 |
| attgacagca | tcgtggagct | tgtttgcaaa | acccttcggg | gcataaacag | tcgccacccc | 720 |
| agcttggcct | tcaaggcagg | tgaatcatcc | atgataatgg | aaatagaact | ccagagccag | 780 |
| gtgctggatg | ccatgaacta | tgtcctttac | gaccaactga | agttcaaggg | gaatcgaatg | 840 |
| gattactata | tgccctcaa | cttatatatg | catcaggttt | tgattcgcag | aacaggaatc | 900 |
| ccaatcagca | tgtctctgct | ctatttgaca | attgctcggc | agttgggagt | cccactggag | 960 |
| cctgtcaact | tcccaagtca | cttcttatta | aggtggtgcc | aaggcgcaga | agggcgacc | 1020 |
| ctggacatct | tgactacat | ctacatagat | gcttttggga | aggcaagca | gctgacagtg | 1080 |
| aaagaatgcg | agtacttgat | cggccagcac | gtgactgcag | cactgtatgg | ggtggtcaat | 1140 |
| gtcaagaagg | tgttacagag | aatggtggga | aacctgttaa | gcctggggaa | gcgggaaggc | 1200 |
| atcgaccagt | cataccagct | cctgagagac | tcgctggatc | tctatctggc | aatgtacccg | 1260 |
| gaccaggtgc | agcttctcct | cctccaagcc | aggctttact | tccacctggg | aatctggcca | 1320 |
| gagaaggtgc | ttgacatcct | ccagcacatc | caaaccctag | accgggggca | gcacggggcg | 1380 |
| gtgggctacc | tggtgcagca | cactctagag | cacattgagc | gcaaaaagga | ggaggtgggc | 1440 |
| gtagaggtga | agctgcgctc | cgatgagaag | cacagagatg | tctgctactc | catcgggctc | 1500 |
| attatgaagc | ataagaggta | tggctataac | tgtgtgatct | acggctggga | ccccaccttgc | 1560 |
| atgatgggac | acgagtggat | ccggaacatg | aacgtccaca | gcctgccgca | cggccaccac | 1620 |
| cagccttttct | ataacgtgct | ggtggaggac | ggctcctgtc | gatacgcagc | ccaagaaaac | 1680 |
| ttggaatata | acgtggagcc | tcaagaaatc | tcacccctg | acgtgggacg | ctatttctca | 1740 |
| gagtttactg | gcactcacta | catcccaaac | gcagagctgg | agatccggta | tccagaagat | 1800 |

-continued

```
ctggagtttg tctatgaaac ggtgcagaat atttacagtg caaagaaaga gaacatagat    1860
gagtaa                                                               1866
```

<210> SEQ ID NO 16
<211> LENGTH: 621
<212> TYPE: PRT
<213> ORGANISM: human

<400> SEQUENCE: 16

```
Met Ala Ala Ala Val Asp Ser Ala Met Glu Val Val Pro Ala Leu
1               5                   10                  15

Ala Glu Glu Ala Ala Pro Glu Val Ala Gly Leu Ser Cys Leu Val Asn
            20                  25                  30

Leu Pro Gly Glu Val Leu Glu Tyr Ile Leu Cys Cys Gly Ser Leu Thr
        35                  40                  45

Ala Ala Asp Ile Gly Arg Val Ser Ser Thr Cys Arg Arg Leu Arg Glu
    50                  55                  60

Leu Cys Gln Ser Ser Gly Lys Val Trp Lys Glu Gln Phe Arg Val Arg
65                  70                  75                  80

Trp Pro Ser Leu Met Lys His Tyr Ser Pro Thr Asp Tyr Val Asn Trp
                85                  90                  95

Leu Glu Glu Tyr Lys Val Arg Gln Lys Ala Gly Leu Glu Ala Arg Lys
            100                 105                 110

Ile Val Ala Ser Phe Ser Lys Arg Phe Phe Ser Glu His Val Pro Cys
        115                 120                 125

Asn Gly Phe Ser Asp Ile Glu Asn Leu Glu Gly Pro Glu Ile Phe Phe
    130                 135                 140

Glu Asp Glu Leu Val Cys Ile Leu Asn Met Glu Gly Arg Lys Ala Leu
145                 150                 155                 160

Thr Trp Lys Tyr Tyr Ala Lys Lys Ile Leu Tyr Tyr Leu Arg Gln Gln
                165                 170                 175

Lys Ile Leu Asn Asn Leu Lys Ala Phe Leu Gln Gln Pro Asp Asp Tyr
            180                 185                 190

Glu Ser Tyr Leu Glu Gly Ala Val Tyr Ile Asp Gln Tyr Cys Asn Pro
        195                 200                 205

Leu Ser Asp Ile Ser Leu Lys Asp Ile Gln Ala Gln Ile Asp Ser Ile
    210                 215                 220

Val Glu Leu Val Cys Lys Thr Leu Arg Gly Ile Asn Ser Arg His Pro
225                 230                 235                 240

Ser Leu Ala Phe Lys Ala Gly Glu Ser Ser Met Ile Met Glu Ile Glu
                245                 250                 255

Leu Gln Ser Gln Val Leu Asp Ala Met Asn Tyr Val Leu Tyr Asp Gln
            260                 265                 270

Leu Lys Phe Lys Gly Asn Arg Met Asp Tyr Tyr Asn Ala Leu Asn Leu
        275                 280                 285

Tyr Met His Gln Val Leu Ile Arg Arg Thr Gly Ile Pro Ile Ser Met
    290                 295                 300

Ser Leu Tyr Leu Thr Ile Ala Arg Gln Leu Gly Val Pro Leu Glu
305                 310                 315                 320

Pro Val Asn Phe Pro Ser His Phe Leu Leu Arg Trp Cys Gln Gly Ala
                325                 330                 335

Glu Gly Ala Thr Leu Asp Ile Phe Asp Tyr Ile Tyr Ile Asp Ala Phe
            340                 345                 350
```

```
Gly Lys Gly Lys Gln Leu Thr Val Lys Glu Cys Glu Tyr Leu Ile Gly
            355                 360                 365

Gln His Val Thr Ala Ala Leu Tyr Gly Val Val Asn Val Lys Lys Val
        370                 375                 380

Leu Gln Arg Met Val Gly Asn Leu Leu Ser Leu Gly Lys Arg Glu Gly
385                 390                 395                 400

Ile Asp Gln Ser Tyr Gln Leu Leu Arg Asp Ser Leu Asp Leu Tyr Leu
                405                 410                 415

Ala Met Tyr Pro Asp Gln Val Gln Leu Leu Leu Gln Ala Arg Leu
            420                 425                 430

Tyr Phe His Leu Gly Ile Trp Pro Glu Lys Val Leu Asp Ile Leu Gln
        435                 440                 445

His Ile Gln Thr Leu Asp Pro Gly Gln His Gly Ala Val Gly Tyr Leu
    450                 455                 460

Val Gln His Thr Leu Glu His Ile Glu Arg Lys Lys Glu Val Gly
465                 470                 475                 480

Val Glu Val Lys Leu Arg Ser Asp Glu Lys His Arg Asp Val Cys Tyr
                485                 490                 495

Ser Ile Gly Leu Ile Met Lys His Lys Arg Tyr Gly Tyr Asn Cys Val
            500                 505                 510

Ile Tyr Gly Trp Asp Pro Thr Cys Met Met Gly His Glu Trp Ile Arg
        515                 520                 525

Asn Met Asn Val His Ser Leu Pro His Gly His His Gln Pro Phe Tyr
    530                 535                 540

Asn Val Leu Val Glu Asp Gly Ser Cys Arg Tyr Ala Ala Gln Glu Asn
545                 550                 555                 560

Leu Glu Tyr Asn Val Glu Pro Gln Glu Ile Ser His Pro Asp Val Gly
                565                 570                 575

Arg Tyr Phe Ser Glu Phe Thr Gly Thr His Tyr Ile Pro Asn Ala Glu
            580                 585                 590

Leu Glu Ile Arg Tyr Pro Glu Asp Leu Glu Phe Val Tyr Glu Thr Val
        595                 600                 605

Gln Asn Ile Tyr Ser Ala Lys Lys Glu Asn Ile Asp Glu
    610                 615                 620

<210> SEQ ID NO 17
<211> LENGTH: 3242
<212> TYPE: DNA
<213> ORGANISM: human

<400> SEQUENCE: 17
atgcgtccaa tgcgaatttt tgtgaatgat gaccgccatg tgatggcaaa gcattcttcc      60
gtttatccaa cacaagagga gctggaggca gtccagaaca tggtgtccca cacggagcgg     120
gcgctcaaag ctgtgtccga ctggatagac gagcaggaaa aggtagcag cgagcaggca     180 gagtccgata catgatgtgt gcccccagag gacgacagta agaagggc tgggaacag       240 aagacggagc acatgaccag aaccctgcgg ggagtgatgc gggtgggcct ggtggcaaag     300
tgcctcctac tcaagggga cttggatctg gagctggtgc tgctgtgtaa ggagaagccc     360
acaaccgccc tcctggacaa ggtggccgac aacctggcca tccagcttgc tgctgtaaca     420
gaagacaagt acgaaatact gcaatctgtc gacgatgctg cgattgtgat aaaaacaca      480 aaagagcctc cattgtccct gaccatccac ctgacatccc ctgttgtcag agaagaaatg     540
gagaaagtat tagctggaga aacgctatca gtcaacgacc ccccggacgt tctggacagg     600
```

-continued

| | |
|---|---|
| cagaaatgcc ttgctgcctt ggcgtccctc cgacacgcca agtggttcca ggccagagcc | 660 |
| aacgggctga agtcttgtgt cattgtgatc cgggtcttga gggacctgtg cactcgcgtg | 720 |
| cccacctggg gtcccctccg aggctggcct ctcgagctcc tgtgtgagaa atccattggc | 780 |
| acggccaaca gaccgatggg tgctggcgag gccctgcgga gagtgctgga gtgcctggcg | 840 |
| tcgggcatcg tgatgccaga tggttctggc atttatgacc cttgtgaaaa agaagccact | 900 |
| gatgctattg ggcatctaga cagacagcaa cgggaagata tcacacagag tgcgcagcac | 960 |
| gcactgcggc tcgctgcctt cggccagctc cataaagtcc taggcatgga ccctctgcct | 1020 |
| tccaagatgc ccaagaaacc aaagaatgaa acccagtgg actacaccgt tcagatccca | 1080 |
| ccaagcacca cctatgccat tacgcccatg aaacgcccaa tggaggagga cggggaggag | 1140 |
| aagtcgccca gcaaaaagaa gaagaagatt cagaagaaag aggagaaggc agagcccccc | 1200 |
| caggctatga atgccctgat gcggttgaac cagctgaagc cagggctgca gtacaagctg | 1260 |
| gtgtcccaga ctgggcccgt ccatgccccc atctttacca tgtctgtgga ggttgatggc | 1320 |
| aattcattcg aggcctctgg gccctccaaa agacggcca agctgcacgt ggccgttaag | 1380 |
| gtgttacagg acatgggctt gccgacgggt gctgaaggca gggactcgag caaggggag | 1440 |
| gactcggctg aggagaccga ggcgaagcca gcagtggtgg cccctgcccc agtggtagaa | 1500 |
| gctgtctcca cccctagtgc ggcctttccc tcagatgcca ctgccgagca ggggccgatc | 1560 |
| ctgacaaagc acggcaagaa cccagtcatg gagctgaacg agaagaggcg tgggctcaag | 1620 |
| tacgagctca tctccgagac cggggcagc acgacaagc gcttcgtcat ggaggtcgaa | 1680 |
| gtggatggac agaagttcca aggtgctggt tccaacaaaa aggtggcgaa ggcctacgct | 1740 |
| gctcttgctg ccctagaaaa gcttttccct gacacccctc tcgcccttga tgccaacaaa | 1800 |
| aagaagagag ccccagtacc cgtcagaggg ggaccgaaat ttgctgctaa gccacataac | 1860 |
| cctggcttcg gcatgggagg ccccatgcac aacgaagtgc ccccacccc caaccttcga | 1920 |
| gggcggggaa gaggcgggag catccgggga cgagggcgcg ggcgaggatt tggtggcgcc | 1980 |
| aaccatggag gctacatgaa tgccggtgct gggtatggaa gctatgggta cggaggcaac | 2040 |
| tctgcgacag caggctacag tcagttctac agcaacggag ggcattctgg gaatgccagt | 2100 |
| ggcggtggcg gcggggcgg tggtggctcc tccggctatg gctcctacta ccaaggtgac | 2160 |
| aactacaact caccggtgcc cccaaaacac gctgggaaga agcagccgca cggggggccag | 2220 |
| cagaagccct cctacggctc gggctaccag tcccaccagg gccagcagca gtcctacaac | 2280 |
| cagagcccct acagcaacta tggccctcca cagggcaagc agaaaggcta taaccatgga | 2340 |
| caaggcagct actcctactc gaactcctac aactctcccg ggggcggggg cggatccgac | 2400 |
| tacaactacg agagcaaatt caactacagt ggtagtggag gccgaagcgg cgggaacagc | 2460 |
| tacggctcag gcgggcatc ctacaaccca gggtcacacg ggggctacgg cggaggttct | 2520 |
| gggggcggct cctcatacca aggcaaacaa ggaggctact cacagtcgaa ctacaactcc | 2580 |
| ccggggtccg gccagaacta cagtggccct cccagctcct accagtcctc acaaggcggc | 2640 |
| tatggcagaa acgcagacca cagcatgaac taccagtaca gataagcccc cgcggggcgg | 2700 |
| agatttctac cttctgcact tactccccat cagaagatcg agttttatgc atcacagtta | 2760 |
| acatgtcagc tggccctcca ggcccccgcc cccatcccgt ccacgttgct gtgtcgtgag | 2820 |
| gtgcagcggg tcaccctgtg gcccgtcctg tgacccatat ttagccgtgt ttgggactcc | 2880 |
| gtgtcttcaa tggtttgtta gttgccatta caactttgtc tgggtagagt ttttgagttt | 2940 |
| ttgcagttca gtatccctct gtctattcac acttcgtgtt agtggtaact cagtttgtct | 3000 |

-continued

```
ttaaatagtt acagaaggga tacgtcattt gttaatgctt ttgtgaagtg agttaaacga    3060
gctttctgta ttttaatgct ttagtgtttc agttttata agtgaagatt ttattttaaa    3120
aaccagtggg aaagagtggg gggtttcttt ttatgtctgg gtcattcagg cagtacatct    3180
gaattaagct gaatgtagac aaataaagaa aaacaaaact aaaaaaaaaa aaaaaaaaa    3240 aa                                                                   3242
```

<210> SEQ ID NO 18
<211> LENGTH: 894
<212> TYPE: PRT
<213> ORGANISM: human

<400> SEQUENCE: 18

```
Met Arg Pro Met Arg Ile Phe Val Asn Asp Asp Arg His Val Met Ala
 1               5                  10                  15

Lys His Ser Ser Val Tyr Pro Thr Gln Glu Glu Leu Glu Ala Val Gln
            20                  25                  30

Asn Met Val Ser His Thr Glu Arg Ala Leu Lys Ala Val Ser Asp Trp
        35                  40                  45

Ile Asp Glu Gln Glu Lys Gly Ser Ser Glu Gln Ala Gly Ser Asp Asn
    50                  55                  60

Met Asp Val Pro Pro Glu Asp Ser Lys Glu Gly Ala Gly Glu Gln
65                  70                  75                  80

Lys Thr Glu His Met Thr Arg Thr Leu Arg Gly Val Met Arg Val Gly
                85                  90                  95

Leu Val Ala Lys Cys Leu Leu Leu Lys Gly Asp Leu Asp Leu Glu Leu
            100                 105                 110

Val Leu Leu Cys Lys Glu Lys Pro Thr Thr Ala Leu Leu Asp Lys Val
        115                 120                 125

Ala Asp Asn Leu Ala Ile Gln Leu Ala Ala Val Thr Glu Asp Lys Tyr
    130                 135                 140

Glu Ile Leu Gln Ser Val Asp Asp Ala Ala Ile Val Ile Lys Asn Thr
145                 150                 155                 160

Lys Glu Pro Pro Leu Ser Leu Thr Ile His Leu Thr Ser Pro Val Val
                165                 170                 175

Arg Glu Glu Met Glu Lys Val Leu Ala Gly Glu Thr Leu Ser Val Asn
            180                 185                 190

Asp Pro Pro Asp Val Leu Asp Arg Gln Lys Cys Leu Ala Ala Leu Ala
        195                 200                 205

Ser Leu Arg His Ala Lys Trp Phe Gln Ala Arg Ala Asn Gly Leu Lys
    210                 215                 220

Ser Cys Val Ile Val Ile Arg Val Leu Arg Asp Leu Cys Thr Arg Val
225                 230                 235                 240

Pro Thr Trp Gly Pro Leu Arg Gly Trp Pro Leu Glu Leu Leu Cys Glu
                245                 250                 255

Lys Ser Ile Gly Thr Ala Asn Arg Pro Met Gly Ala Gly Glu Ala Leu
            260                 265                 270

Arg Arg Val Leu Glu Cys Leu Ala Ser Gly Ile Val Met Pro Asp Gly
        275                 280                 285

Ser Gly Ile Tyr Asp Pro Cys Glu Lys Glu Ala Thr Asp Ala Ile Gly
    290                 295                 300

His Leu Asp Arg Gln Gln Arg Glu Asp Ile Thr Gln Ser Ala Gln His
305                 310                 315                 320
```

```
Ala Leu Arg Leu Ala Ala Phe Gly Gln Leu His Lys Val Leu Gly Met
            325                 330                 335

Asp Pro Leu Pro Ser Lys Met Pro Lys Lys Pro Lys Asn Glu Asn Pro
            340                 345                 350

Val Asp Tyr Thr Val Gln Ile Pro Pro Ser Thr Thr Tyr Ala Ile Thr
            355                 360                 365

Pro Met Lys Arg Pro Met Glu Glu Asp Gly Glu Glu Lys Ser Pro Ser
            370                 375                 380

Lys Lys Lys Lys Lys Ile Gln Lys Lys Glu Glu Lys Ala Glu Pro Pro
385                 390                 395                 400

Gln Ala Met Asn Ala Leu Met Arg Leu Asn Gln Leu Lys Pro Gly Leu
                405                 410                 415

Gln Tyr Lys Leu Val Ser Gln Thr Gly Pro Val His Ala Pro Ile Phe
            420                 425                 430

Thr Met Ser Val Glu Val Asp Gly Asn Ser Phe Glu Ala Ser Gly Pro
            435                 440                 445

Ser Lys Lys Thr Ala Lys Leu His Val Ala Val Lys Val Leu Gln Asp
            450                 455                 460

Met Gly Leu Pro Thr Gly Ala Glu Gly Arg Asp Ser Ser Lys Gly Glu
465                 470                 475                 480

Asp Ser Ala Glu Glu Thr Glu Ala Lys Pro Ala Val Val Ala Pro Ala
                485                 490                 495

Pro Val Val Glu Ala Val Ser Thr Pro Ser Ala Ala Phe Pro Ser Asp
            500                 505                 510

Ala Thr Ala Glu Gln Gly Pro Ile Leu Thr Lys His Gly Lys Asn Pro
            515                 520                 525

Val Met Glu Leu Asn Glu Lys Arg Arg Gly Leu Lys Tyr Glu Leu Ile
            530                 535                 540

Ser Glu Thr Gly Gly Ser His Asp Lys Arg Phe Val Met Glu Val Glu
545                 550                 555                 560

Val Asp Gly Gln Lys Phe Gln Gly Ala Gly Ser Asn Lys Lys Val Ala
                565                 570                 575

Lys Ala Tyr Ala Ala Leu Ala Ala Leu Glu Lys Leu Phe Pro Asp Thr
            580                 585                 590

Pro Leu Ala Leu Asp Ala Asn Lys Lys Lys Arg Ala Pro Val Pro Val
            595                 600                 605

Arg Gly Gly Pro Lys Phe Ala Ala Lys Pro His Asn Pro Gly Phe Gly
            610                 615                 620

Met Gly Gly Pro Met His Asn Glu Val Pro Pro Pro Asn Leu Arg
625                 630                 635                 640

Gly Arg Gly Arg Gly Gly Ser Ile Arg Gly Arg Gly Arg Gly Arg Gly
            645                 650                 655

Phe Gly Gly Ala Asn His Gly Gly Tyr Met Asn Ala Gly Ala Gly Tyr
            660                 665                 670

Gly Ser Tyr Gly Tyr Gly Gly Asn Ser Ala Thr Ala Gly Tyr Ser Gln
            675                 680                 685

Phe Tyr Ser Asn Gly Gly His Ser Gly Asn Ala Ser Gly Gly Gly Gly
            690                 695                 700

Gly Gly Gly Gly Gly Ser Ser Gly Tyr Gly Ser Tyr Tyr Gln Gly Asp
705                 710                 715                 720

Asn Tyr Asn Ser Pro Val Pro Pro Lys His Ala Gly Lys Lys Gln Pro
            725                 730                 735
```

```
-continued

His Gly Gly Gln Gln Lys Pro Ser Tyr Gly Ser Gly Tyr Gln Ser His
            740             745             750

Gln Gly Gln Gln Gln Ser Tyr Asn Gln Ser Pro Tyr Ser Asn Tyr Gly
            755             760             765

Pro Pro Gln Gly Lys Gln Lys Gly Tyr Asn His Gly Gln Gly Ser Tyr
        770             775             780

Ser Tyr Ser Asn Ser Tyr Asn Ser Pro Gly Gly Gly Gly Gly Ser Asp
785             790             795                         800

Tyr Asn Tyr Glu Ser Lys Phe Asn Tyr Ser Gly Ser Gly Gly Arg Ser
                805             810             815

Gly Gly Asn Ser Tyr Gly Ser Gly Gly Ala Ser Tyr Asn Pro Gly Ser
            820             825             830

His Gly Gly Tyr Gly Gly Ser Gly Gly Gly Ser Ser Tyr Gln Gly
            835             840             845

Lys Gln Gly Gly Tyr Ser Gln Ser Asn Tyr Asn Ser Pro Gly Ser Gly
        850             855             860

Gln Asn Tyr Ser Gly Pro Pro Ser Ser Tyr Gln Ser Ser Gln Gly Gly
865             870             875             880

Tyr Gly Arg Asn Ala Asp His Ser Met Asn Tyr Gln Tyr Arg
                885             890
```

TUMOR ASSOCIATED ANTIGENS AND METHODS OF USING THE SAME

RELATED APPLICATIONS

This application claims the benefit of U.S. Provisional Patent Application Nos. 60/278,253, filed Mar. 23, 2001, and 60/278,237, filed Mar. 24, 2001, the disclosures of which are incorporated by reference herein.

STATEMENT AS TO RIGHTS TO INVENTIONS MADE UNDER FEDERALLY SPONSORED RESEARCH AND DEVELOPMENT

This work was supported by U.S. Government grants numbers CA82724 and CA84359, awarded by the National Institutes of Health, and U.S. Department of Defense Grant Number OC970002. The U.S. Government may have certain rights in the invention.

BACKGROUND OF THE INVENTION

Ovarian carcinoma remains one of the most lethal gynecologic malignancies. It has been reported to be the fifth most common cancer and the fourth leading cause of cancer mortality among women in the United States (see Maller et al., *SEER Cancer Statistics Review.* 1973–1990, Bethesda, Md., National Cancer Institute(1993)).

Due to the lack of powerful diagnostic tests and also to the absence of any overt symptoms, early detection of ovarian cancer is difficult. In approximately two-thirds of patients, the disease is at an advanced stage (i.e., stage III or IV) at the time of diagnosis (see Boring et al., *Ca. Cancer J. Clin.* 44:7–26 (1994); Coppleson et al., *Gynecologic Oncology: Fundamental Principles and Clinical Practice,* 2nd ed, London, Churchill Livingstone Press (1992); Hung et al., "The Female Reproductive System: Cell Lines from Tumor of the Human Ovary and Uterus", in Hay et al., *Atlas of Human Tumor Cell Lines,* Academic Press, San Diego, pp 359–386(1994)). Currently, diagnostic assays are limited to a few markers. Numerous studies on ovarian carcinomas have reported genetic alterations in oncogenes and tumor suppressor genes (see, e.g., Piver et al., *Semin. Oncol.* 18: 177–85 (1991)). Specifically, amplification or activation of the oncogenes HER-2/neu, K-ras and c-myc, as well as inactivation of the tumor suppressor genes p53, BRCA1 and the human mismatch repair genes hMLH1, hMSH2, hPMS1 and hPMS2, have been detected in ovarian cancers. It has been reported that mutation of the p53 gene occurs in about 30–50% of ovarian cancers (see, e.g., Berchuck et al., *Am. J. Obstet. Gynecol.* 170:246–52 (1994)). p53 gene mutations are common in a variety of other tumors, however.

Accordingly, there exists a need to identify new markers associated with ovarian cancer and other epithelial cancers. The present invention satisfies this and other needs.

BRIEF SUMMARY OF THE INVENTION

The present invention provides methods and compositions for the diagnosis of hyperproliferative disease and autoimmune disease. Tumor associated antigens, nucleic acids encoding them and antibodies to the tumor associated antigens are provided for the diagnosis of hyperproliferative disease, such as, for example, ovarian cancer, breast cancer, lung cancer, colorectal cancer, and other epithelial cancers, and for the diagnosis of autoimmune disease.

In one aspect, methods for the prognosis or diagnosis of hyperproliferative disease are provided. The methods include obtaining a sample from the subject, the sample including antibodies, and contacting the sample with at least one tumor associated antigen. The tumor associated antigen can be ZFP161, Ubiquilin-1, HOX-B6, IFI27, YB-1, KIAA0136, Osteonectin, F-box only protein 21, and/or ILF3. Complex formation is detected between the tumor associated antigen and the antibodies in the sample. Complex formation can indicate a prognosis or diagnosis of hyperproliferative disease. The subject can be a mammal, such as a human.

The sample can be blood, serum, ascites fluid, mucosal fluid, cervical wash, nipple aspirate fluid, stool, urine, saliva, tears, sputum, and the like. Complex formation can be detected by, for example, Western blot assay, radioimmunoassay, ELISA, sandwich immunoassay, immunoprecipitation assay, precipitin reaction, gel diffusion precipitin reaction, immunodiffusion assay, agglutination assay, complement-fixation assay, immunoradiometric assay, fluorescent immunoassay or protein A immunoassay. The hyperproliferative disease can be an epithelial cancer, such as ovarian cancer, breast cancer, lung cancer, colorectal cancer, and the like.

In another aspect, methods for prognosis or diagnosis of autoimmune disease in a subject are provided. The methods include obtaining a sample from the subject, the sample including antibodies. The sample is contacted with at least one tumor associated antigen. The tumor associated antigen can be, for example, ZFP161, Ubiquilin-1, HOX-B6, IFI27, YB-1, KIAA0136, Osteonectin, F-box only protein 21, and/or ILF3. Complex formation between the tumor associated antigen and the antibodies in the sample is then detected. Complex formation can indicate a prognosis or diagnosis of autoimmune disease. The subject can be a mammal, such as a human.

The sample can be, for example, blood, serum, ascites fluid, mucosal fluid, cervical wash, nipple aspirate fluid, stool, urine or saliva. Complex formation can be detected by, for example, Western blot assay, radioimmunoassay, ELISA, sandwich immunoassay, immunoprecipitation assay, precipitin reaction, gel diffusion precipitin reaction, immunodiffusion assay, agglutination assay, complement-fixation assay, immunoradiometric assay, fluorescent immunoassay or protein A immunoassay.

The autoimmune disease can be, for example, rheumatoid arthritis, graft versus host disease, systemic lupus erythromatosis (SLE), scleroderma, multiple sclerosis, diabetes, organ rejection, inflammatory bowel disease, psoriasis, and the like.

In yet another aspect, methods for prognosis or diagnosis of hyperproliferative disease in a subject are provided. The methods include obtaining a sample from the subject and contacting the sample with at least one antibody to a tumor associated antigen. The tumor associated antigen can be, for example, ZFP161, Ubiquilin-1, HOX-B6, IFI27, YB-1, KIAA0136, Osteonectin, F-box only protein 21, and/or ILF3. Complex formation between the antibody and tumor associated antigen in the sample is then detected. Complex formation can indicate a prognosis or diagnosis of hyperproliferative disease.

The subject can be a mammal, such as a human. The sample can be tissue, cells, plasma, serum, ascites fluid, mucosal fluid, cervical wash, nipple aspirate fluid, spinal fluid, lymph fluid, the external sections of the skin, respiratory, intestinal, and genitourinary tracts, tears, saliva, hair, tumors, organs, stool, urine, tears, sputum, and the like.

Complex formation can be detected by, for example, Western blot assay, radioimmunoassay, ELISA, sandwich immunoassay, immunoprecipitation assay, precipitin reaction, gel diffusion precipitin reaction, immunodiffusion assay, agglutination assay, complement-fixation assay, immunoradiometric assay, fluorescent immunoassay and/or protein A immunoassay. The hyperproliferative disease can be epithelial cancer, such as, for example, ovarian cancer, breast cancer, lung cancer, colorectal cancer, and the like.

In a related aspect, additional methods for prognosis or diagnosis of hyperproliferative disease in a subject are provided. The methods include contacting an array of probe molecules stably associated with a surface of a solid support with a sample of target nucleic acids under hybridization conditions sufficient to produce a hybridization pattern. The probe molecules can be nucleic acids encoding at least a fragment of at least one of ZFP161, Ubiquilin-1, HOX-B6, IFI27, YB-1, KIAA0136, Osteonectin, F-box only protein 21, and/or ILF3. The hybridization pattern is detected to determine whether the subject has a hyperproliferative disease. The hybridization pattern can indicate a prognosis or diagnosis of hyperproliferative disease. The sample can be from, for example, ovary, lung, breast or the colorectal tract of the subject. The sample can also be tissue, cells, plasma, serum, ascites fluid, mucosal fluid, cervical wash, nipple aspirate fluid, spinal fluid, lymph fluid, the external sections of the skin, respiratory, intestinal, and genitourinary tracts, tears, sputum, saliva, hair, tumors, organs, stool, or urine. The hyperproliferative disease can be epithelial cancer, such as, for example, ovarian cancer, lung cancer, breast cancer or colorectal cancer. The target nucleic acids can be labeled in one embodiment.

A kit for detecting antibodies to a tumor associated antigen is also provided. The kit includes at least one tumor associated antigen. The tumor associated antigen can be, for example, ZFP161, Ubiquilin-1, HOX-B6, IFI27, YB-1, KIAA0136, Osteonectin, F-box only protein 21, and/or ILF3. The kit typically further includes anti-human antibody. In one embodiment, the tumor associated antigen is labeled; in another embodiment, the anti-human antibody is labeled.

A kit for detecting expression of tumor associated antigen genes is also provided. The kit can include nucleic acid primers to a tumor associated antigen nucleic acids. The tumor associated antigen nucleic acid can be, for example, ZFP161, Ubiquilin-1, HOX-B6, IFI27, YB-1, KIAA0136, Osteonectin, F-box only protein 21, and/or ILF3. The kit typically further includes a polynucleotide polymerase, nucleotides, and/or a buffer. The kit can optionally further include an array of probe molecules for use in a hybridization assay.

Definitions

Prior to setting forth the invention in more detail, it may be helpful to a further understanding thereof to set forth definitions of certain terms as used hereinafter. Unless defined otherwise, all technical and scientific terms used herein have the same meaning as commonly understood by one of ordinary skill in the art to which this invention belongs. Only exemplary methods and materials are described, and any methods and materials similar to those described herein can be used in the practice or testing of the present invention. For purposes of the present invention, the following terms are defined below.

The terms "polynucleotide" and "nucleic acid" refer to a polymer composed of a multiplicity of nucleotide units (ribonucleotide or deoxyribonucleotide or related structural variants) linked via phosphodiester bonds. A polynucleotide or nucleic acid can be of substantially any length, typically from about six (6) nucleotides to about $10^9$ nucleotides or larger. Polynucleotides and nucleic acids include RNA, cDNA, genomic DNA, synthetic forms, and mixed polymers, both sense and antisense strands, and can also be chemically or biochemically modified or can contain non-natural or derivatized nucleotide bases, as will be readily appreciated by the skilled artisan. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, and the like), charged linkages (e.g., phosphorothioates, phosphorodithioates, and the like), pendent moieties (e.g., polypeptides), intercalators (e.g., acridine, psoralen, and the like), chelators, alkylators, and modified linkages (e.g., alpha anomeric nucleic acids, and the like). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The term "oligonucleotide" refers to a polynucleotide of from about six (6) to about one hundred (100) nucleotides or more in length. Thus, oligonucleotides are a subset of polynucleotides. Oligonucleotides can be synthesized, for example, on an automated oligonucleotide synthesizer (for example, those manufactured by Applied BioSystems (Foster City, Calif.)), according to specifications provided by the manufacturer.

The term "primer" as used herein refers to a polynucleotide, typically an oligonucleotide, whether occurring naturally, as in an enzyme digest, or whether produced synthetically, which acts as a point of initiation of polynucleotide synthesis when used under conditions in which a primer extension product is synthesized. A primer can be single-stranded or double-stranded.

The term "polypeptide" refers to a polymer of amino acids and its equivalent and does not refer to a specific length of the product; thus, peptides, oligopeptides and proteins are included within the definition of a polypeptide. A "fragment" refers to a portion of a polypeptide having at least 6 contiguous amino acids, typically 8–10 contiguous amino acids, more typically at least 20 contiguous amino acids, still more typically at least 50 contiguous amino acids of the tumor associated antigen polypeptide. A derivative is a polypeptide having conservative amino acid substitutions, as compared with another sequence. Derivatives further include, for example, glycosylations, acetylations, phosphorylations, and the like. Further included within the definition of "polypeptide" are, for example, polypeptides containing one or more analogs of an amino acid (e.g., unnatural amino acids, and the like), polypeptides with substituted linkages as well as other modifications known in the art, both naturally and non-naturally occurring, as more fully described infra.

The terms "amino acid" or "amino acid residue", as used herein, refer to naturally occurring L amino acids or to D amino acids. The commonly used one- and three-letter abbreviations for amino acids are used herein (see, e.g., Alberts et al., *Molecular Biology of the Cell*, Garland Publishing, Inc., New York (3d ed. 1994)).

The term "heterologous" refers to a nucleic acid or polypeptide from a different source, such as a tissue, organism or species, as compared with another nucleic acid or polypeptide.

The term "isolated" refers to a nucleic acid, polypeptide or antibody that has been removed from its natural cellular environment. An isolated nucleic acid is typically at least partially purified from other cellular nucleic acids, polypeptides and other constituents.

The terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence, as measured using one of the following sequence comparison algorithms, or by visual inspection.

The phrase "substantially identical," in the context of two nucleic acids or polypeptides, refers to two or more sequences or subsequences that have at least 60%, typically 80%, most typically 90–95% nucleotide or amino acid residue identity, when compared and aligned for maximum correspondence, as measured using one of the following sequence comparison algorithms, or by visual inspection. An indication that two polypeptide sequences are "substantially identical" is that one polypeptide is immunologically reactive with antibodies raised against the second polypeptide.

"Similarity" or "percent similarity" in the context of two or polypeptide sequences, refer to two or more sequences or subsequences that are the same or have a specified percentage of amino acid residues or conservative substitutions thereof, that are the same, when compared and aligned for maximum correspondence, as measured using one of the following sequence comparison algorithms, or by visual inspection. By way of example, a first amino acid sequence can be considered similar to a second amino acid sequence when the first amino acid sequence is at least 60%, 70%, 75%, 80%, 85%, 90%, or even 95% identical, or conservatively substituted, to the second amino acid sequence when compared to an equal number of amino acids as the number contained in the first sequence, or when compared to an alignment of polypeptides that has been aligned by a computer similarity program known in the art, as discussed below.

The term "substantial similarity" in the context of polypeptide sequences indicates that the polypeptide comprises a sequence with at least 70% sequence identity to a reference sequence, or typically 80%, or more typically 85% sequence identity or 90% sequence identity over a comparison window of about 10–20 amino acid residues. In the context of amino acid sequences, "substantial similarity" further includes conservative substitutions of amino acids. Thus, a polypeptide is substantially similar to a second polypeptide, for example, where the two peptides differ only by one or more conservative substitutions.

The term "conservative substitution," when describing a polypeptide, refers to a change in the amino acid composition of the polypeptide that does not substantially alter the polypeptide's activity. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not substantially alter activity. Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, *Proteins*, W. H. Freeman and Company (1984).) In addition, individual substitutions, deletions or additions that alter, add or delete a single amino acid or a small percentage of amino acids in an encoded sequence are also "conservative substitutions."

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm of Smith and Waterman (*Adv. Appl. Math.* 2:482 (1981)), by the homology alignment algorithm of Needleman and Wunsch (*J. Mol. Biol.* 48:443 (1970)), by the search for identity method of Pearson and Lipman (*Proc. Natl. Acad. Sci. USA* 85:2444 (1988)), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., *Current Protocols in Molecular Biology*, 4th ed., John Wiley and Sons, New York (1999)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng and Doolittle (*J. Mol. Evol.* 35:351–60 (1987)). The method used is similar to the CLUSTAL method described by Higgins and Sharp (*Gene* 73:237–44 (1988); *CABIOS* 5:151–53 (1989)). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described in Altschul et al. (*J. Mol. Biol.* 215:403–10 (1990)). Software for performing BLAST analyses is publicly available through the National Center for Biotechnology Information (http:// www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin and Altschul, *Proc. Natl. Acad. Sci. USA* 90:5873–87 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is typically less than about 0.1, more typically less than about 0.01, and most typically less than about 0.001. Another indication that two nucleic acids are substantially identical is that the two molecules hybridize specifically to each other under stringent conditions.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

"Stringent hybridization conditions" and "stringent hybridization wash conditions" in the context of nucleic acid hybridization experiments, such as Southern and northern hybridization, are sequence-dependent, and are different under different environmental parameters. Longer sequences hybridize specifically at higher temperatures. An extensive guide to the hybridization of nucleic acids is found in Tijssen, *Laboratory Techniques in Biochemistry and Molecular Biology—Hybridization with Nucleic Acid Probes* (part I, chapter 2 "Overview of principles of hybridization and the strategy of nucleic acid probe assays," Elsevier, N.Y. (1993), which is incorporated by reference herein). Generally, highly stringent hybridization and wash conditions are selected to be about 5° C. lower than the thermal melting point ($T_m$) for the specific sequence at a defined ionic strength and pH. Typically, under "stringent conditions," a probe will hybridize to its target subsequence, but not to other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide in 4–6×SSC or SSPE at 42° C., or 65–68° C. in aqueous solution containing 4–6×SSC or SSPE. An example of highly stringent wash conditions is 0.15 M NaCl at 72° C. for about 15 minutes. An example of stringent wash conditions is a 0.2×SSC wash at 65° C. for 15 minutes. (See generally Sambrook et al., *Molecular Cloning, A Laboratory Manual,* 3rd ed., Cold Spring Harbor Publish., Cold Spring Harbor, N.Y. (2001), which is incorporated by reference herein.) Often, a high stringency wash is preceded by a low stringency wash to remove background probe signal. An example of medium stringency wash for a duplex of, for example, more than 100 nucleotides, is 1×SSC at 45° C. for 15 minutes. An example of a low stringency wash for a duplex of, for example, more than 100 nucleotides, is 4–6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code.

The term "immunologically cross-reactive" means that a polypeptide, fragment, derivative or analog is capable of competitively inhibiting the binding of an antibody to its antigen.

The term "sample" generally indicates a specimen of tissue, cells, plasma, serum, ascites fluid, mucosal fluid, cervical wash, nipple aspirate fluid, spinal fluid, lymph fluid, the external sections of the skin, respiratory, intestinal, and genitourinary tracts, tears, saliva, hair, tumors, organs, stool, urine, other material of biological origin that contains antibodies, polypeptide and/or polynucleotides, or in vitro cell culture constituents of any of these. A sample can further be semi-purified or purified forms of antibodies, polypeptides and/or polynucleotides. A sample can be isolated from a mammal, such as a human, an animal, any other organism as well as in vitro culture constituents of any of these.

The term "proliferation" refers to activities such as growth, reproduction, change in gene expression, transformation, and other changes in cell state. "Hyper-proliferation" refers to an increase in one or more proliferative activities, as compared with normal cells or tissue. "Hyperproliferative disease" refers to a disease, condition, or disorder associated with hyperproliferation of cells or tissues in a subject. Diseases involving hyper-proliferation include, but are not limited to, cancer, malignancies, premalignant conditions (e.g., hyperplasia, metaplasia, dysplasia), benign tumors, hyperproliferative disorders, benign dysproliferative disorders, autoimmune diseases, and the like.

The term "antibody" refers to a polypeptide substantially encoded by an immunoglobulin gene or immunoglobulin genes, or fragments thereof, that specifically binds and recognizes an analyte (antigen). Immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain has a variable region of about 100 to 110 or more amino acids primarily responsible for antigen recognition. The terms "variable light chain" (or "$V_L$") and "variable heavy chain" (or "$V_H$") refer to these light and heavy chains, respectively.

Antibodies exist, for example, as intact immunoglobulins or as a number of well characterized antigen-binding fragments produced by digestion with various peptidases. For example, pepsin digests an antibody below the disulfide linkages in the hinge region to produce an F(ab')$_2$ fragment, a dimer of Fab which itself is a light chain joined to VH—CH1 by a disulfide bond. The F(ab')$_2$ fragment can be reduced under mild conditions to break the disulfide linkage in the hinge region, thereby converting the F(ab')$_2$ dimer into an Fab' monomer. The Fab' monomer is essentially an Fab with part of the hinge region (see *Fundamental Immunology*, Third Edition, W. E. Paul (ed.), Raven Press, N.Y. (1993)). While various antibody fragments are defined in terms of the digestion of an intact antibody, one of skill will appreciate that such fragments can be synthesized de novo either chemically or by utilizing recombinant DNA methodology. Thus, the term antibody, as used herein, also includes antibody fragments, such as a single chain antibody, an antigen binding F(ab')$_2$ fragment, an antigen binding Fab' fragment, an antigen binding Fab fragment, an antigen binding Fv fragment, a single heavy chain or a chimeric antibody. Such antibodies can be produced by the modification of whole antibodies or synthesized de novo using recombinant DNA methodologies. (See, e.g., Harlow and Lane, *Using Antibodies, A Laboratory Manual*, Cold Spring Harbor Laboratory, New York (1999), the disclosure of which is incorporated by reference herein.)

DESCRIPTION OF THE SPECIFIC EMBODIMENTS

The present invention provides methods and compositions for the diagnosis of hyperproliferative disease and/or autoimmune disease. Tumor associated antigens, nucleic acids encoding them and antibodies to the tumor associated antigens are provided for the diagnosis of hyperproliferative disease, such as, for example, ovarian cancer, breast cancer, lung cancer, colorectal cancer, and other epithelial cancers, and/or for the diagnosis of autoimmune disease.

Tumor Associated Antigen Nucleic Acids

In one aspect, nucleic acids encoding tumor associated antigen are provided as markers of hyperproliferative disease or autoimmune disease. Such tumor associated antigen nucleic acids can include, for example, proteins, fragments, derivatives and analogs thereof, the function (e.g., expression or activity) of which is altered in cells associated with hyperproliferative disease and/or autoimmune disease. The tumor associated antigen nucleic acids can also encode polypeptides of normal function, but which are differentially immunogenic in the context of cells associated with hyperproliferative disease and/or autoimmune disease as compared with normal epithelial cells of the same tissue or cell type.

The tumor associated antigen nucleic acids can include, for example, nucleic acids encoding a zinc finger-containing protein ZFP161, Ubiquilin-1, HOX-B6, IFI27, YB-1, KIAA0136, Osteonectin, F-box only protein 21, and/or ILF3. The tumor associated antigen nucleic acids can further include those encoding the tumor suppressor gene p53 and/or the cancer-testis antigen NY-ESO-1. Such tumor associated antigen nucleic acids can include nucleic acids from human and non-human mammals, such as, for example, porcine, bovine, feline, equine, and/or canine species, as well as primate species.

In some embodiments, the tumor associated antigen nucleic acids correspond to human nucleic acid sequences encoding ZFP161, Ubiquilin-1, HOX-B6, IFI27, YB-1, KIAA0136, Osteonectin, F-box only protein 21, and/or ILF3. The tumor associated antigen nucleic acids can further include those encoding the tumor suppressor gene p53 and/or the cancer-testis antigen NY-ESO-1. In specific embodiments, the tumor associated antigen nucleic acids correspond to the following nucleic acids, which are referenced by their National Center for Biotechnology Information Unigene accession numbers: ZFP161 (Hs.156000; ZFP161); Ubiquilin-1 (Hs.9589; UBQLN1); HOX-B6 (Hs.98428; HOXB6); IFI27 (Hs.278613; IFI27); YB-1 (Hs.74497; NSEP1); KIAA0136 (Hs.70359; KIAA0316); Osteonectin (Hs.111779; SPARC); F-box only protein 21 (Hs.184227; FBXO21); ILF3 (Hs.256583; ILF3), or the coding regions thereof. The tumor associated antigen nucleic acids can additionally correspond to the nucleic acids encoding p53 (Hs.1846; TP53); NY-ESO-1 (Hs.167379; CTAG1), or the coding regions thereof. (All of these sequences are incorporated by reference herein in their entirety.)

The invention also provides fragments of tumor associated antigen nucleic acids comprising at least 6 contiguous nucleotides (i.e., a hybridizable portion); in other embodiments, the nucleic acids comprise contiguous nucleotides of at least 10 nucleotides, 15 nucleotides, 25 nucleotides, 50 nucleotides, 100 nucleotides, 150 nucleotides, 200 nucleotides, or 250 nucleotides of a tumor associated antigen nucleic acid sequence. The nucleic acids can also be smaller than 35, 200 or 250 nucleotides in length. Nucleic acids can be single or double stranded. As used herein, a "nucleic acid encoding a fragment or portion of a tumor associated antigen polypeptide" refers to a nucleic acid encoding only the recited fragment or portion of the tumor associated antigen polypeptide and not the other contiguous portions of the tumor associated antigen polypeptide as a continuous sequence. Fragments of tumor associated antigen nucleic acids comprising regions conserved between other tumor associated antigen nucleic acids, of the same or different species, are also provided. Nucleic acids encoding one or more tumor associated antigen domains are also provided.

The invention also relates to nucleic acids hybridizable to or complementary to the foregoing sequences. In specific aspects, nucleic acids are provided which comprise a sequence complementary to at least 10, 15, 25, 50, 100, 200, or 250 nucleotides of a tumor associated antigen gene, or a portion thereof. In a specific embodiment, a nucleic acid which is hybridizable to a tumor associated antigen nucleic acid, or to a nucleic acid encoding a tumor associated antigen derivative, under conditions of low, medium or high stringency is provided. Low, moderate and high stringency conditions are well known to those of skill in the art, and will vary predictably depending on the base composition of the particular nucleic acid sequence and on the specific organism from which the nucleic acid sequence is derived. For guidance regarding such conditions see, for example, Sambrook et al. (supra); and Ausubel et al. (supra) (both of which are incorporated by reference herein).

Nucleic acids encoding derivatives and analogs of tumor associated antigen proteins, and tumor associated antigen antisense nucleic acids are additionally provided. Derivatives of the tumor associated antigen sequences include those nucleotide sequences encoding substantially the same amino acid sequences as found in native tumor associated antigen proteins, and those encoded amino acid sequences with functionally equivalent amino acids (e.g., conservative substitutions).

Tumor associated antigen nucleic acids can be obtained by standard procedures known in the art (e.g., by chemical synthesis, by cDNA cloning, by the cloning of genomic DNA, by PCR amplification, and the like. (See, e.g., Sambrook et al., supra; Glover (ed.), *DNA Cloning: A Practical Approach*, MRL Press, Ltd., Oxford, U.K. Vol. I, II (1995); Ausubel et al, supra; the disclosures of which are incorporated by reference herein.) The nucleic acids can also identified by searching nucleic databases for nucleic acid sequences that are substantially similar to known tumor associated antigen nucleic acid sequences.

Tumor Associated Antigen Polypeptides

In another aspect, the invention relates to tumor associated antigen polypeptide markers of hyperproliferative disease, such as epithelial cancers. The invention further relates to tumor associated antigen polypeptide markers of autoimmune disease. Such tumor associated antigen polypeptides can include, for example, proteins, fragments, derivatives and analogs thereof, the function (e.g., expression or activity) of which is altered in cells associated with hyperproliferative disease and/or autoimmune disease. The tumor associated antigens also include polypeptides of normal function, but which are differentially immunogenic in cells associated with hyperproliferative disease and/or autoimmune disease as compared with normal epithelial cells of the same tissue or cell type.

Tumor associated antigen polypeptides include, for example, Ubiquilin-1, IFI27, HOX-B6, ZFP161, YB-1, KIAA0136, Osteonectin, F-box only protein 21, or ILF3, alone or in combination with p53, NY-ESO-1, and/or fragments, derivatives or analogs of any of these, as further discussed below. The tumor associated antigens include polypeptides from human and non-human mammals, such as, for example, porcine, bovine, feline, equine, and/or canine species, as well as other primate species.

In some embodiments, the tumor associated antigen polypeptides are human Ubiquilin-1, IFI27, HOX-B6, ZFP161, YB-1, KIAA0136, Osteonectin, F-box only protein 21, and/or ILF3, alone or in combination with p53, NY-ESO-1, and/or fragments, derivatives or analogs thereof. In specific embodiments, the tumor associated antigens have the deduced amino acid sequences of the following tumor associated antigen nucleic acid sequences (which are referenced by their National Center for Biotechnology Information Unigene accession numbers): Ubiquilin-1 (Hs.9589; UBQLN1); IFI27 (Hs.278613; IFI27) HOX-B6 (Hs.98428; HOXB6); ZFP161 (Hs.156000; ZFP161) YB-1 (Hs.74497; NSEP1); KIAA0136 (Hs.70359; KIAA0316); Osteonectin (Hs.111779; SPARC); F-box only protein 21 (Hs.184227; FBXO21); and/or ILF3 (Hs.256583; ILF3). The tumor associated antigens can also have the deduced amino acid sequences of p53 (Hs.1846; TP53) and/or NY-ESO-1 (Hs.167379; CTAG1), or fragments thereof.

Tumor associated antigen polypeptide derivatives include naturally-occurring amino acid sequence variants as well as these altered by substitution, addition or deletion of one or more amino acid residues. Tumor associated antigen polypeptide derivatives include, but are not limited to, those containing as a primary amino acid sequence all or part of the amino acid sequence of a tumor associated antigen polypeptide, including altered sequences in which one or more functionally equivalent amino acid residues (e.g., a conservative substitution) are substituted for residues within the sequence, resulting in a silent change.

In another aspect, a polypeptide consisting of or comprising a fragment of a tumor associated antigen polypeptide having at least 10 contiguous amino acids of the tumor associated antigen polypeptide is provided. In other embodiments, the fragment has at least 20 or 50 contiguous amino acids of the tumor associated antigen polypeptide. The fragments can also be smaller than 35, 100 or 200 amino acids.

Fragments, derivatives or analogs of tumor associated antigen polypeptides include, but are not limited to, those molecules comprising regions that are substantially similar to tumor associated antigen polypeptide or fragments thereof (e.g., in various embodiments, at least 70%, 75%, 80%, 90%, or even 95% identity or similarity over an amino acid sequence of identical size), or when compared to an aligned sequence in which the alignment is done by a computer sequence comparison/alignment program known in the art, or whose coding nucleic acid is capable of hybridizing to a tumor associated antigen nucleic acid, under high stringency, moderate stringency, or low stringency conditions (supra).

Tumor associated antigen polypeptide fragments, derivatives and analogs can be produced by various methods known in the art. The manipulations which result in their production can occur at the gene or protein level. For example, the cloned tumor associated antigen nucleic acids can be modified by any of numerous strategies known in the art (see, e.g., Sambrook et al., supra), such as making conservative substitutions, deletions, insertions, and the like. The sequence can be cleaved at appropriate sites with restriction endonuclease(s), followed by further enzymatic modification if desired, isolated, and ligated in vitro. In the production of the tumor associated antigen nucleic acids encoding a fragment, derivative or analog of a tumor associated antigen polypeptide, the modified nucleic acid typically remains in the proper translational reading frame, so that the reading frame is not interrupted by translational stop signals or other signals which interfere with the synthesis of the tumor associated antigen fragment, derivative or analog. Tumor associated antigen nucleic acids can also be mutated in vitro or in vivo to create and/or destroy translation, initiation and/or termination sequences. The tumor associated antigen-encoding nucleic acid can also be mutated to create variations in coding regions and/or to form new restriction endonuclease sites or destroy preexisting ones and to facilitate further in vitro modification. Any technique for mutagenesis known in the art can be used, including but not limited to, chemical mutagenesis, in vitro site-directed mutagenesis (Hutchison et al., *J. Biol. Chem.* 253:6551–60 (1978); Sambrook et al., supra), and the like.

Manipulations of the tumor associated antigen polypeptide sequence can also be made at the polypeptide level. Included within the scope of the invention are tumor associated antigen polypeptide fragments, derivatives or analogs which are differentially modified during or after synthesis (e.g., in vivo or in vitro translation). Such modifications include conservative substitution, glycosylation, acetylation, phosphorylation, amidation, derivatization by known protecting/blocking groups, proteolytic cleavage, linkage to an antibody molecule or other cellular ligand, and the like. Any of numerous chemical modifications can be carried out by known techniques, including, but not limited to, specific chemical cleavage (e.g., by cyanogen bromide), enzymatic cleavage (e.g., by trypsin, chymotrypsin, papain, V8 protease, and the like); modification by, for example, $NaBH_4$ acetylation, formylation, oxidation and reduction, metabolic synthesis in the presence of tunicamycin, and the like.

In addition, tumor associated antigen polypeptides, fragments, derivatives and analogs can be chemically synthesized. For example, a peptide corresponding to a portion, or fragment, of a tumor associated antigen polypeptide, which comprises a desired domain, or which mediates a desired activity in vitro, can be synthesized by use of chemical synthetic methods using, for example, an automated peptide synthesizer. Furthermore, if desired, nonclassical amino acids or chemical amino acid analogs can be introduced as a substitution or addition into the tumor associated antigen polypeptide sequence. Non-classical amino acids include but are not limited to the D-isomers of the common amino acids, α-amino isobutyric acid, 4-aminobutyric acid, 2-amino butyric acid, λ-amino butyric acid, 6-amino hexanoic acid, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, selenocysteine, fluoro-amino acids, designer amino acids such as β-methyl amino acids, C α-methyl amino acids, N α-methyl amino acids, and amino acid analogs in general. Furthermore, the amino acid can be D (dextrorotary) or L (levorotary).

In a specific embodiment, the tumor associated antigen polypeptide, fragment, derivative or analog is a chimeric, or fusion, protein comprising a tumor associated antigen polypeptide, fragment, derivative or antigen thereof (typically containing at least a domain or motif of the tumor associated antigen polypeptide, or at least 10 contiguous amino acids of the tumor associated antigen polypeptide) joined at its amino- or carboxy-terminus via a peptide bond to an amino acid sequence of a different protein. In one embodiment, such a chimeric protein is produced by recombinant expression of a nucleic acid encoding the protein. The chimeric product can be made by ligating the appropriate nucleic acid sequences, encoding the desired amino acid sequences, to each other in the proper coding frame and expressing the chimeric product by methods commonly known in the art. Alternatively, the chimeric product can be made by protein synthetic techniques (e.g., by use of an automated peptide synthesizer).

The production and use of tumor associated antigen polypeptides, fragments, derivatives and analogs thereof are also within the scope of the present invention. In a specific embodiment, the polypeptide, fragment, derivative or analog is immunogenic or antigenic (e.g., that can be recognized by an antibody specific for the tumor associated antigen polypeptide) by immune cell such as T cells. As one example, such fragments, derivatives or analogs which have the desired immunogenicity or antigenicity can be used, for example, in immunoassays, for immunization, and the like. A specific embodiment relates to a tumor associated antigen fragment that can be bound by an anti-tumor associated antigen antibody, such as an antibody in a sample from a subject. Fragments, derivatives or analogs of tumor associated antigen can be tested for the desired activity by methods known in the art.

Tumor associated antigen polypeptides can be isolated and purified by standard methods including chromatography (e.g., ion exchange, affinity, sizing column chromatography, high pressure liquid chromatography, and like), centrifugation, differential solubility, or by any other standard technique for the purification of proteins. The functional properties can be evaluated using any suitable assay as described herein or otherwise known to the skilled artisan. Alternatively, once a tumor associated antigen polypeptide produced by a recombinant host cell is identified, the amino acid sequence of the polypeptide can be deduced from the nucleotide sequence of the chimeric gene contained in the recombinant host cell. As a result, the protein can be synthesized by standard chemical methods known in the art (see, e.g., Hunkapiller et al., *Nature* 310:105–11 (1984); Stewart and Young, *Solid Phase Peptide Synthesis,* 2nd Ed., Pierce Chemical Co., Rockford, Ill., (1984)).

In another alternate embodiment, native tumor associated antigen polypeptides can be purified from natural sources by standard methods such as those described above (e.g., immunoaffinity purification). In a specific embodiment of the present invention, tumor associated antigen polypeptides, whether produced by recombinant DNA techniques, by chemical synthetic methods or by purification of native polypeptides include, but are not limited to, those containing as a primary amino acid sequence all or part of the amino acid sequence of tumor associated antigen polypeptide, as well as fragments, derivatives and analogs thereof.

Antibodies to Tumor Associated Antigens

Antibodies against tumor associated antigens are also provided. The antibodies are typically immunospecific for tumor associated antigens, such as, for example, Ubiquilin-1, IFI27, HOX-B6, ZFP161, YB-1, KIAA0136, Osteonectin, F-box only protein 21, and/or ILF3, or fragments, derivative or analogs thereof. The antibodies can further include those against p53 or NY-ESO-1, or fragments, derivative or analogs thereof. In specific embodiments, the antibodies are immunospecific for human tumor associated antigens.

Tumor associated antigen antibodies include, but are not limited to, polyclonal antibodies, monoclonal antibodies, chimeric antibodies, single chain antibodies, antigen binding antibody fragments (e.g., Fab, Fab', $F(ab')_2$, Fv, or hypervariable regions), bi-specific antibodies, and an Fab expression library. In some embodiments, polyclonal and/or monoclonal antibodies to a tumor associated antigen are produced. In other embodiments, antibodies to a domain of a tumor associated antigen are produced. In yet other embodiments, fragments of a tumor associated antigen that are identified as immunogenic are used as immunogens for antibody production.

Various procedures known in the art can be used for the production of polyclonal antibodies. For the production of such antibodies, various host animals (including, but not limited to, rabbits, mice, rats, sheep, goats, camels, and the like) can be immunized by injection with a tumor associated antigen, fragment, derivative or analog. Various adjuvants can be used to increase the immunological response, depending on the host species. Such adjuvants include, for example, Freund's adjuvant (complete and incomplete), mineral gels such as aluminum hydroxide, surface active substances such as lysolecithin, pluronic polyols, polyanions, peptides, oil emulsions, keyhole limpet hemocyanins, dinitrophenol, and other adjuvants, such as BCG (bacille Calmette-Guerin) and *Corynebacterium parvum*.

For preparation of monoclonal antibodies directed toward a tumor associated antigen, any technique that provides for the production of antibody molecules by continuous cell lines in culture can be used. Such techniques include, for example, the hybridoma technique originally developed by Kohler and Milstein (see, e.g., *Nature* 256:495–97 (1975)), the trioma technique (see, e.g., Hagiwara and Yuasa, *Hum. Antibodies Hybridomas* 4:15–19 (1993); Hering et al., *Biomed. Biochim. Acta* 47:211–16 (1988)), the human B-cell hybridoma technique (see, e.g., Kozbor et al., *Immunology Today* 4:72 (1983)), and the EBV-hybridoma technique to produce human monoclonal antibodies (see, e.g., Cole et al., In: *Monoclonal Antibodies and Cancer Therapy*, Alan R. Liss, Inc., pp. 77–96 (1985)). Human antibodies can be used and can be obtained by using human hybridomas (see, e.g., Cote et al., *Proc. Natl. Acad. Sci. USA* 80:2026–30 (1983)) or by transforming human B cells with EBV virus in vitro (see, e.g., Cole et al., supra).

Further to the invention, "chimeric" antibodies (see, e.g., Morrison et al., *Proc. Natl. Acad. Sci. USA* 81:6851–55 (1984); Neuberger et al., *Nature* 312:604–08 (1984); Takeda et al., *Nature* 314:452–54 (1985)) can be prepared. Such chimeric antibodies are typically prepared by splicing the genes (of one species) for an antibody molecule specific for tumor associated antigen together with genes from another species of antibody molecule of appropriate biological activity. It can be desirable to transfer the antigen binding regions (e.g., Fab', F(ab')$_2$, Fab, Fv, or hypervariable regions) of antibodies from one species into the framework of an antibody from another species by recombinant DNA techniques to produce a chimeric molecule. Methods for producing such "chimeric" molecules are generally well known and described in, for example, U.S. Pat. Nos. 4,816,567; 4,816,397; 5,693,762; and 5,712,120; PCT Patent Publications WO 87/02671 and WO 90/00616; and European Patent Publication EP 239 400 (the disclosures of which are incorporated by reference herein). In a specific embodiment, a human monoclonal antibody or portion(s) thereof can be identified by screening a human B-cell cDNA library for nucleic acid molecules that encode antibodies that specifically bind to a tumor associated antigen according to the method generally set forth by Huse et al. (*Science* 246: 1275–81 (1989)). The nucleic acid molecule can then be cloned and amplified to obtain sequences that encode the antibody (or antigen-binding domain) of the desired specificity. Phage display technology offers another technique for selecting antibodies that bind to tumor associated antigens, fragments, derivatives or analogs thereof. (See, e.g., International Patent Publications WO 91/17271 and WO 92/01047; Huse et al., supra.)

According to another aspect of the invention, techniques described for the production of single chain antibodies (see, e.g., U.S. Pat. Nos. 4,946,778 and 5,969,108) can be used. An additional aspect of the invention utilizes the techniques described for the construction of a Fab expression library (see, e.g., Huse et al., supra) to allow rapid and easy identification of monoclonal Fab fragments with the desired specificity for tumor associated antigens, fragments, derivatives, or analogs thereof.

Antibody fragments that contain the idiotype of the molecule can be generated by known techniques. For example, such fragments include but are not limited to, the F(ab')$_2$ fragment which can be produced by pepsin digestion of the antibody molecule, the Fab' fragments which can be generated by reducing the disulfide bridges of the F(ab')$_2$ fragment, the Fab fragments which can be generated by treating the antibody molecule with papain and a reducing agent, and Fv fragments. Recombinant Fv fragments can also be produced in eukaryotic cells using, for example, the methods described in U.S. Pat. No. 5,965,405 (the disclosure of which is incorporated by reference herein).

In another embodiment, bi-specific antibodies are provided. Bi-specific antibodies can be monoclonal antibodies that have binding specificities for at least two different antigens. For example, one of the binding specificities can be for a tumor associated antigen and the other one is for any other antigen. Alternatively, one specificity is for a first tumor associated antigen, while the other specificity is for a second, different tumor associated antigen.

Methods for making bi-specific antibodies are known in the art. Traditionally, the recombinant production of bi-specific antibodies is based on the co-expression of two immunoglobulin heavy-chain/light-chain pairs, where the two heavy chains have different specificities (see, e.g., Milstein and Cuello, *Nature* 305:537–39 (1983), the disclosure of which is incorporated by reference herein). Because of the random assortment of immunoglobulin heavy and light chains, these hybridomas (quadromas) produce a potential mixture of different antibody molecules, some of which have the desired bi-specific structure. The purification of the correct molecule is usually accomplished by affinity chromatography steps. Similar procedures are disclosed in PCT Patent Publication WO 93/08829, and in Traunecker et al. (*EMBO J.* 10:3655–59 (1991)) (the disclosures of which are incorporated by reference herein).

Antibody variable domains with the desired binding specificities (antibody-antigen combining sites) can be fused to immunoglobulin constant domain sequences. The fusion typically is with an immunoglobulin heavy-chain constant domain, comprising at least part of the hinge, CH2, and CH3 regions. The first heavy-chain constant region (CH1) containing the site necessary for light-chain binding is usually present in at least one of the fusions. DNAs encoding the immunoglobulin heavy-chain fusions and, if desired, the immunoglobulin light chain, are inserted into separate expression vectors, and are co-transfected into a suitable host organism. For further details of generating bi-specific antibodies see, for example, Suresh et al (*Methods in Enzymology* 121:210 (1986), the disclosure of which is incorporated by reference herein).

In the production of antibodies, screening for the desired antibody can be accomplished by techniques known in the art (e.g., ELISA (enzyme-linked immunosorbent assay)). (See, e.g., Harlow and Lane, supra.)

Diagnostics

Methods and compositions for diagnosis of hyperproliferative disease or autoimmune disease are also provided. Such methods and compositions can be used to detect, prognose, diagnose, or monitor hyperproliferative disease or autoimmune disease associated with aberrant changes in tumor associated antigen expression, activity and/or immunogenicity.

In a typical embodiment, a sample can be obtained from a subject. The sample can be contacted with at least one tumor associated antigen, or antibody to at least one tumor associated antigen. The tumor associated antigen is typically ZFP161, Ubiquilin-1, HOX-B6, IFI27, YB-1, KIAA0136, Osteonectin, F-box only protein 21, and/or ILF3. Complex formation of the tumor associated antigen or antibody with antibody or tumor associated antigen in the sample can be detected. In certain embodiments, complex formation from the sample can be compared with complex formation from a control sample (e.g., normal tissue or cells, tissue or cells not having aberrant changes in tumor associated antigen expression, activity and/or immunogenicity, serum from a healthy subject, and the like).

A prognosis or diagnosis of the presence of hyperproliferative disease or autoimmune disease in the subject can be indicated by the presence of antigen:antibody complexes. Such a positive diagnosis can optionally indicate a need for further testing, such as, for example, sonograph, ultrasound, biopsy, exploratory surgery, and the like. Thus, in some embodiments, the methods and composition can comprise a screen or prescreen for detection of hyperproliferative and/or autoimmune disease.

Tumor associated antigen polypeptides (including fragments, derivatives, and analogs thereof), tumor associated antigen nucleic acids (and sequences complementary thereto), and anti-tumor associated antigen antibodies have uses in diagnostics to detect, prognose, diagnose, or monitor hyperproliferative disease or autoimmune disease. Such hyperproliferative diseases include, but are not limited to, epithelial cancers, such as ovarian cancer, breast cancer, lung cancer, colorectal cancer, and the like. As will be appreciated by the skilled artisan, although the following discussion exemplifies method and compositions for use in the diagnosis, detection, prognosis, or monitoring of hyperproliferative disease, such assays can also be used to diagnose, detect, prognose, or monitor autoimmune disease. The autoimmune disease can be, for example, rheumatoid arthritis, graft versus host disease, systemic lupus erythromatosis (SLE), scleroderma, multiple sclerosis, diabetes, organ rejection, inflammatory bowel disease, psoriasis, and the like.

In one aspect, immunoassays are used to detect antibodies in a subject ("autoimmune antibodies") against one or more of the tumor associated antigens. For example, immunoassays can be used to detect autoimmune antibodies against Ubiquilin-1, IFI27, HOX-B6, ZFP161, YB-1, KIAA0136, Osteonectin, F-box only protein 21, and/or ILF3 in a sample from a subject. The immunoassays can also be used to detect p53, and/or NY-ESO-1. The presence of antibody to one or more of these tumor associated antigen is an indication of a hyperproliferative disease in the subject.

Immunoassays which can be used to detect such autoimmune antibodies include, for example, competitive and non-competitive assay systems such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, and the like. (See, e.g., Harlow and Lane, *Using Antibodies, A Laboratory Manual*, Cold Spring Harbor Laboratory, New York (1999).)

Immunoassays can be carried out, for example, by contacting a subject sample with tumor associated antigen polypeptide under conditions such that immunospecific binding (complex formation) can occur, and detecting or measuring the amount of any immunospecific binding of antibody to the tumor associated antigen. The tumor associated antigen can be used to detect the presence (e.g., high, low or absence) of antibody against tumor associated antigens in blood, serum, ascites fluid, mucosal fluid (e.g., cervical fluids), and the like, in a sample from a subject.

For example, autoimmune antibodies in a subject sample can be detected by the following method. The tumor associated antigen (or a fragment, derivative and/or analog thereof) is immobilized on a matrix. Then, a sample to be assayed (e.g., blood, serum, ascites fluid, mucosal fluid, and the like) is added and allowed to react at a temperature suitable for immunospecific binding (e.g., from about 4° C. to about 40° C.).

Following the binding reaction, the matrix is washed and then a secondary antibody is added to the reaction mixture; the secondary antibody typically immunospecifically binds to the subject antibodies (e.g., anti-human antibodies). The secondary antibody is allowed to react with autoimmune antibodies bound to the tumor associated antigen on the matrix.

The secondary antibody can be detectably labeled with, for example, a fluorescent substance, a chromogenic substance, a chemiluminescent substance, an enzyme, a radioisotope, by biotinyl moieties, and the like. Examples of detectable labels include, but are not limited to, the following: radioisotopes (e.g., $^3$H, $^{14}$C, $^{32}$P, $^{35}$S, $^{125}$I, $^{131}$I, and the like), fluorescent molecules (e.g., fluorescein isothiocyanate (FITC), rhodamine, phycoerythrin (PE), phycocyanin, allophycocyanin, ortho-phthaldehyde, fluorescamine, peridininchlorophyll a (PerCP), Cy3 (indocarbocyanine), Cy5 (indodicarbocyanine), lanthanide phosphors, and the like), enzymes (e.g., horseradish peroxidase, β-galactosidase, luciferase, alkaline phosphatase), biotinyl groups, and the like. In some embodiments, detectable labels are attached by spacer arms of various lengths to reduce potential steric hindrance.

The reaction mixture is then washed to remove unbound secondary antibody, and the secondary antibody bound to the matrix is detected. For example, bound, labeled secondary antibody can be detected by standard colorimetric, radioactive, photometric and/or fluorescent detection means. Detection reagents can be used, if needed. For fluorescent labels, signal can be detected by, for example, a scanning confocal microscope in photon counting mode. Appropriate scanning devices are described by, for example, U.S. Pat. Nos. 5,578,832 and 5,631,734 (both incorporated by reference herein). For antibodies labeled with biotin, the reaction can be treated with the appropriate streptavidin-conjugate (e.g., streptavidin-horseradish peroxidase, streptavidin-alkaline phosphatase, streptavidin-luciferase, and the like) and then treated with the appropriate reagents for calorimetric or photometric detection. For radiolabeled antibody, signal can be detected using a scintillation counter, phosphoimager or similar device. Alternatively, the secondary antibody can be unlabeled, and the presence of autoimmune antibodies against a tumor associated antigen is detected using a labeled tertiary antibody.

Any suitable matrix can be used for immobilizing the tumor associated antigen. For example, for ELISA, the tumor associated antigen can be immobilized on ELISA plates, microtiter plates, and the like. In one embodiment, histidine-tagged tumor associated antigen is bound to H is Sorb ELISA plates (Quiagen). Alternatively, the tumor associated antigen can be immobilized in a sandwich assay.

Autoimmune antibody can also be detected in a conventional Western blotting assay, such as by immobilizing at least one tumor associated antigen to a solid support matrix, such as, for example, nitrocellulose membrane, nylon membrane, PVDF membrane, and the like.

The tumor associated antigens can also be immobilized on other matrices. The matrices can have virtually any possible structural configuration so long as the immobilized antigen is capable of binding to an antibody. Thus, the support configuration can be spherical, as in a bead, or cylindrical, as in the inside surface of a test tube, or the external surface of a rod. Alternatively, the surface can be flat such as a sheet, test strip, and the like.

Suitable matrices include, for example, gel beads (e.g., Sepharose 4B, Sepharose 6B (Pharmacia Fine Chemicals (Sweden))), dextran gel (e.g., Sephadex G-75, Sephadex G-100, Sephadex G-200 (Pharmacia Fine Chemicals (Sweden))), polyacrylamide gel (e.g., Bio-Gel P-30, Bio-Gel P-60, Bio-Gel P-100 (Bio-Rad Laboratories USA)), cellulose beads (e.g., Avicel (Asahi Chemical Industry Co. Ltd.)), ion exchange cellulose (e.g., diethylaminoethylcellulose, carboxymethylcellulose), physical adsorbents (e.g., glass (glass beads, glass rods, aminoalkyl glass beads, aminoalkyl glass rods)), silicone flakes, styrenic resin (e.g., polystyrene beads, polystyrene particles), immunoassay plates (e.g., Nunc (Denmark)), ion exchange resin (e.g., weakly acidic cation exchange resin (e.g., Amberlite IRC-5 (Rohm & Haas Company (U.S.A.)), Zeo-Karb 226 (Permutit (West Germany)), and weakly basic anion exchange resin (e.g., Amberlite IR-4B, Dowex 3 (Dow Chemical (U.S.A.)))), and the like.

Immunoassays to detect autoimmune antibody in a subject sample can also be performed, for example, by contacting a subject sample with a labeled tumor associated antigen polypeptide under conditions such that immunospecific binding can occur (complex formation), and detecting or measuring the amount of immunospecific complex formation. Such immunoassays can include, for example, immunoprecipitations and RIA's.

Tumor associated antigen can be labeled with, for example, a fluorescent substance, a chromogenic substance, a chemiluminescent substance, an enzyme, a radioisotope, by biotinyl moieties, and the like, as described supra.

Diagnostic assays can also be performed to qualitatively or quantitatively detect tumor associated antigen in a subject sample. For example, immunoassays can be used to detect one or more of the following tumor associated antigens in a subject sample: Ubiquilin-1, IFI27, HOX-B6, ZFP161, YB-1, KIAA0136, Osteonectin, F-box only protein 21, and/or ILF3. The immunoassays can also be used to detect p53, and/or NY-ESO-1 in a sample from a subject.

For example, immunoassays to detect tumor associated antigen can be carried out by a method comprising contacting a sample derived from a subject with an anti-tumor associated antigen antibody under conditions such that immunospecific binding (complex formation) can occur, and detecting or measuring the amount of any immunospecific binding. In a specific aspect, binding of antibody to tissue sections from a subject can be used to detect aberrant (e.g., high, low or absent) levels of tumor associated antigen and/or aberrant tumor associated antigen localization. By "aberrant levels," is meant increased or decreased levels or immunogenicity relative to that present, or a standard level representing that present, in an analogous sample from a samples, a portion of the body or from a subject not having the hyperproliferative disease.

In a specific embodiment, antibody to tumor associated antigen can be used to assay a subject's tissue, serum or other biological sample for the presence of tumor associated antigen, where an aberrant level or immunogenicity of the tumor associated antigen is an indication of a hyperproliferative disease (e.g., an epithelial cancer). The immunoassays which can be used to detect tumor associated antigen include, for example, competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, and the like. (See, e.g., Harlow and Lane, *Using Antibodies, A Laboratory Manual*, Cold Spring Harbor Laboratory, New York (1999).)

For example, antibodies can be used to quantitatively or qualitatively detect the presence of tumor associated antigens using immunofluorescence techniques employing a fluorescently labeled antibody (see, e.g., supra) coupled with light microscopic, flow cytometric, or fluorimetric detection. Such techniques can be used for the detection of tumor associated antigens that are expressed on the cell surface. Thus, the techniques described herein can be used to detect specific cells, within a population of cells, having altered tumor associated antigen expression or immunogenicity.

Immunoassays can also be employed histologically, as in immunofluorescence or immunoelectron microscopy, for in situ detection of tumor associated antigen. In situ detection can be accomplished by removing a histological sample from a subject, and contacting the sample with a labeled antibody. The antibody is typically contacted with the sample by overlaying the labeled antibody onto the sample. Through the use of such a procedure, the presence of the tumor associated antigen can be determined and/or the distribution of the antigen in the histological sample can be examined. Those of ordinary skill in the art will readily appreciate that any of a wide variety of histological methods (such as staining procedures) can be modified in order to achieve such in situ detection.

In some embodiments, a biological sample from a subject is contacted with and immobilized onto a matrix, such as, for example, nitrocellulose, or other solid support (see supra) which is capable of immobilizing cells, cell particles or polypeptides. The matrix can then be washed with suitable buffers followed by treatment with the labeled antibody. The matrix can then be washed with the buffer to remove unbound antibody. The amount of bound label on the matrix can be detected by conventional means.

Bound, labeled antibody can be detected by standard calorimetric, radioactive, photometric and/or fluorescent detection means. Detection reagents can be used, if needed. For fluorescent labels, signals can be detected by, for example, a scanning confocal microscope in photon counting mode. Appropriate scanning devices are described by, for example, U.S. Pat. Nos. 5,578,832 and 5,631,734 (both incorporated by reference herein). For antibodies labeled with biotin, the reaction can be treated with the appropriate streptavidin-conjugate (e.g., streptavidin-horseradish peroxidase, streptavidin-alkaline phosphatase, streptavidin-luciferase, and the like) and then treated with the appropriate reagents for colorimetric or photometric detection. For radiolabeled antibody, signals can be detected using a scintillation counter, phosphoimager or similar device.

In another aspect, diagnostic assays are provided to detect the expression of tumor associated antigen genes. Tumor associated antigen nucleic acid sequences, or fragments thereof comprising about at least 8 nucleotides, can be used as hybridization probes. Hybridization assays can be used to detect, prognose, diagnose, or monitor hyperproliferative disease associated with aberrant changes in tumor associated antigen expression and/or activity. In particular, such a hybridization assay can be carried out by a method comprising contacting a sample containing nucleic acids (target nucleic acids) with a nucleic acid probe capable of hybridizing to tumor associated antigen nucleic acid, under conditions such that hybridization can occur, and detecting or measuring any resulting hybridization.

In specific embodiments, hyperproliferative disease can be diagnosed, or its suspected presence can be screened for, or a predisposition to develop such disease can be detected, by detecting tumor associated antigen RNA associated with increased or altered expression of the tumor associated antigen. Suitable hybridization assays include, for example, Northern blots, dot blots, RT-PCR, quantitative PCR, and the like.

In a specific embodiment, levels of tumor associated antigen mRNA are detected or measured, in which increased levels indicate that the subject has, or has a predisposition to developing, a hyperproliferative disease. Diagnostic procedures can also be performed in situ directly upon, for example, tissue sections (e.g., fixed and/or frozen) of subject tissue obtained from biopsies or resections, such that no nucleic acid purification is necessary. Tumor associated antigen nucleic acids can be used as probes and/or primers for such in situ procedures (see, e.g., Nuovo, *PCR In Situ Hybridization: Protocols and Applications*, Raven Press, NY (1992), the disclosure of which is incorporated by reference herein).

Diagnostic methods for the detection of tumor associated antigen nucleic acids can also involve, for example, contacting and incubating nucleic acids from a subject sample with one or more labeled nucleic acids, under conditions favorable for the specific annealing of the nucleic acids to their complementary sequences. Typically, the lengths of these nucleic acid reagents are at least 15 to 30 nucleotides. After incubation, all non-annealed nucleic acids are removed. The presence of bound nucleic acids from the sample, if any such molecules exist, is then detected. Using such a detection scheme, the nucleic acid from the tissue or cell type of interest can be immobilized, for example, to a solid support such as a membrane, or a plastic surface such as that on a microtiter plate or polystyrene beads.

Nucleic acid arrays can be used to monitor the expression of tumor associated genes, such as, for example, Ubiquilin-1, IFI27, HOX-B6, ZFP161, YB-1, KIAA0136, Osteonectin, F-box only protein 21, and/or ILF3. Nucleic acid arrays can further be used to detect p53, and/or NY-ESO-1 gene expression. Typically, an array of polynucleotide probes is contacted with a sample of target nucleic acids to produce a hybridization pattern. The binding of the target nucleic acids to one or more probes of the array is then detected to obtain a qualitative and/or quantitative profile of expression of the tumor associated antigen gene.

An array of polynucleotide probes stably associated with the surface of a substantially planar solid support is typically contacted with a sample of target nucleic acids under hybridization conditions sufficient to produce a hybridization pattern of complementary probe/target complexes. A variety of different arrays can be used and are known in the art. The polymeric or probe molecules of the arrays can be polynucleotides or hybridizing derivatives or analogs thereof, including: nucleic acids in which the phosphodiester linkage has been replaced with a substitute linkage, such as phosphorothioate, methylimino, methyl-phosphonate, phosphoramidate, guanidine, and the like; nucleic acids in which the ribose subunit has been substituted, for example, hexose phosphodiester; peptide nucleic acids; and the like. The length of the probes will generally range from about 10 to about 1000 nucleotides. In some embodiments the probes will be oligonucleotides and usually range from about 15 to about 150 nucleotides and more usually from about 15 to about 100 nucleotides in length. In other embodiments the probes will be longer, usually ranging in length from about 150 to about 1000 nucleotides. The probes can be single or double stranded, usually single stranded, and can be PCR fragments amplified from cDNA. The probe molecules on the surface of the substrates will typically correspond to at least one of the tumor associated antigen genes and be positioned on the array at a known locations so that positive hybridization events can be correlated to expression of a particular gene in the physiological source from which the target nucleic acid sample is derived. Because of the manner in which the target nucleic acid sample is generated, as described below, the arrays of probes will generally have sequences that are complementary to the non-template strands of the gene to which they correspond.

The substrates with which the probe molecules are stably associated can be fabricated from a variety of materials, including plastics, ceramics, metals, gels, membranes, glasses, and the like. The arrays can be produced according to any convenient methodology, such as preforming the probes and then stably associating them with the surface of the support or growing the probes directly on the support. A number of different array configurations and methods for their production are known to those of skill in the art and disclosed in, for example, U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637; the disclosures of which are herein incorporated by reference.

The target nucleic acid is typically contacted with the array under conditions sufficient for hybridization of target nucleic acid to probe to occur. Suitable hybridization conditions are well known to those of skill in the art and reviewed in Sambrook et al. (supra) and PCT Patent Publication WO 95/21944 (incorporated by reference herein). For example, low stringency hybridization conditions can be at 50° C. and 6×SSC while hybridization under stringent conditions can be at 50° C. or higher and 0.1×SSC.

In one embodiment, the amount of tumor associated antigen nucleic acids in the sample can be quantitated. (See, e.g., U.S. Pat. No. 6,004,755, the disclosure of which is incorporated by reference herein.) For example, the target nucleic acids in the sample can be end-labeled in a manner such that each of the target nucleic acids in the sample produces a signal of the same specific activity. By generating the same specific activity is meant that each individual target polynucleotide in the sample being assayed is labeled in a manner such that the molecule is capable of providing the same signal (e.g., the same intensity of signal) as every other labeled target in the sample. Each of the target nucleic acids generates a signal of the same specific activity because the number of labeled nucleotide bases in each of the target molecules is either identical or substantially the same.

The label is capable of providing a detectable signal, either directly or through interaction with one or more additional members of a signal producing system. Labels that are directly detectable and that can find use in the subject invention include: fluorescent labels. The fluorescers of interest include fluorescers in which the wavelength of light absorbed by the fluorescer will generally range from about 300 to 900 nm, usually from about 400 to 800 nm. The absorbance maximum will typically occur at a wavelength ranging from about 500 to 800 nm. Specific fluorescers of interest for use in singly labeled primers include, for example, fluorescein, rhodamine, BODIPY, cyanine dyes and the like, and are further described in Smith et al (*Nature* 321:647–79 (1986)). Suitable radioactive isotopes include, for example, $^{35}S$, $^{32}P$, $^{3}H$, etc. Examples of labels that provide a detectable signal through interaction with one or more additional members of a signal producing system include capture moieties that specifically bind to complementary binding pair members, where the complementary binding pair members comprise a directly detectable label moiety, such as a fluorescent moiety as described above. Capture moieties of interest include ligands, such as, for example, biotin where the other member of the signal producing system could be fluorescently labeled streptavidin, and the like.

In some applications, it is desired to analyze populations of target nucleic acids from two or more samples. Such samples can be differentially labeled. Alternatively, targets nucleic acids from different samples are separately contacted to identical probe arrays under conditions of hybridization, typically stringent hybridization conditions, such that labeled nucleic acids hybridize to their complementary probes on the substrate surface, and the target nucleic acids bound to the array separately detected. A set of standard nucleic acid molecules can optionally be used. For example, the standard nucleic acids can be provided by reverse transcribing standard RNA.

Following hybridization, a washing step can be employed to remove non-specifically bound nucleic acid from the support surface, generating a pattern of hybridized nucleic acid on the substrate surface. A variety of wash solutions and protocols for their use are known to those of skill in the art and can be used.

Where the label on the target nucleic acid is not directly detectable, the array can be contacted with the other member(s) of the signal producing system that is being employed. For example, where the label on the target is biotin, the array can be contacted with streptavidin-fluorescer conjugate under conditions sufficient for binding between the specific binding member pairs to occur. Following contact, any unbound members of the signal producing system will then be removed (e.g., by washing). The specific wash conditions employed can depend on the specific nature of the signal producing system that is employed, and will be known to those of skill in the art familiar with the particular signal producing system employed.

The resultant hybridization pattern(s) of target nucleic acids bound to the array can be visualized or detected in a variety of ways, with the particular manner of detection being chosen based on the particular label of the nucleic acid. For example, detection means can include scintillation counting, autoradiography, fluorescence measurement, colorimetric measurement, light emission measurement, and the like.

Prior to detection or visualization, the array of hybridized target/probe complexes can be optionally treated with an endonuclease. The endonuclease degrades single stranded, but not double stranded DNA. A variety of different endonucleases are known and can be used. Such nucleases include, for example, mung bean nuclease, S1 nuclease, and the like.

Following detection or visualization, the hybridization pattern can be used to determine qualitative and/or quantitative information about the expression of tumor associated antigen genes. The hybridization patterns of different samples can be compared with each other, or with a control sample, to identify differences between the patterns. The hybridization arrays can also be used to identify differential gene expression, in the analysis of diseased and normal tissue (e.g., neoplastic and normal tissue), different tissue or subtissue types; and the like.

Kits for diagnostic use are also provided, that comprise in one or more containers a tumor associated antigen, and, optionally, anti-tumor associated antigen antibody. The tumor associated antigen can optionally be labeled (e.g., with a detectable marker, such as, for example, a chemiluminescent, enzymatic, fluorescent, and/or radioactive moiety). Kits for diagnostic use are also provided that comprise in one or more containers an anti-tumor associated antigen antibody, and, optionally, a labeled binding partner to the antibody. Alternatively, the anti-tumor associated antigen antibody can be labeled (with a detectable marker, such as, for example, a chemiluminescent, enzymatic, fluorescent, and/or radioactive moiety).

A kit is also provided that comprises in one or more containers a nucleic acid probe capable of hybridizing to tumor associated antigen RNA. In a specific embodiment, a kit can comprise in one or more containers a pair of primers (e.g., each in the size range of 6–30 nucleotides, or more in length) that are capable of priming amplification (e.g., by polymerase chain reaction (see, e.g., Innis et al., *PCR Protocols*, Academic Press, Inc., San Diego, Calif. (1990)), ligase chain reaction (see, e.g., EP 320,308), use of Qβ replicase, cyclic probe reaction, or other methods known in the art under appropriate reaction conditions, of at least a portion of a tumor associated antigen nucleic acid. A kit can optionally further comprise in a container a predetermined amount of at least one purified tumor associated antigen or nucleic acid, for example, for use as a standard or control.

The following examples are provided merely as illustrative of various aspects of the invention and shall not be construed to limit the invention in any way.

EXAMPLES

Example 1

The following example describes the identification of tumor associated antigens using serum from patients having ovarian cancer.

SEREX Immunoscreening

RNA isolated from ten stage III/IV serous ovarian tumors was pooled and poly-A selected using an mRNA Separator kit from Clontech. Selected mRNA was converted to cDNA with a modified ZAP cDNA synthesis kit (Stratagene) and cloned into lambda TriplEx (Clontech). Prior to screening, serum from stage III ovarian cancer patients was pre-cleared of *E. coli* specific antibodies using an *E. coli* affinity resin (5Prime3Prime) according to the manufacturers instructions. SEREX immunoscreening was performed essentially as described by Tureci et al. (*Hybridoma* 18:23–28 (1999); *Mol. Med. Today* 3:342–49 (1997), both incorporated by reference herein). Briefly, aliquots of the expanded library were plated at $2\times10^3$ PFU/100 mm plate, overlaid with IPTG impregnated nitrocellulose membranes and incubated overnight at 37° C. The following morning, lifts were washed three times in Tris buffered saline (TBS: 20 mM Tris-HCl pH 7.5 and 150 mM NaCl)+0.05% Tween 20, blocked in TBS+1% BSA for 2 hours and exposed to serum diluted 1:200 in TBS/BSA overnight at room temperature. Lifts were washed 3 times in TBS and incubated with an alkaline phosphatase-linked goat anti-human IgG secondary antibody for 45 minutes at room temp. After three washes in TBS, lifts were developed in nitro blue tetrazolium chloride/5-bromo-4-chloro-3-indoyl phosphate (NBT/BCIP) for approximately 5 minutes, stopped in water for 20 minutes and dried. Positive phage plaques were picked and stored in SM buffer (100 mM NaCl, 50 mM Tris-HCl pH 7.5 and 10 mM $MgSO_4$) at 4° C. with a drop of chloroform.

Antigen Validation

The primary clones were validated using a SEREX array protocol. Briefly, a small aliquot of each phage suspension was spotted onto a bacterial lawn in a defined position (an array). Multiple identical plates were constructed with identical phage arrays. Arrays were overlaid with IPTG impregnated nitrocellulose membranes and grown overnight as described for basic SEREX screening. Individual lifts were then exposed to serum from a single normal or cancer patient. In this manner, large numbers of normal and patient sera can be screened for antibodies to a large number of primary clones. Clones that bind serum antibodies present in one or more patient sera and not normal sera are classified as a tumor antigen.

Phage encoding tumor antigens were purified by SEREX screening plates infected with increasing dilutions of phage suspension. Isolated positive plaques were then picked and suspended in SM buffer, with a drop of chloroform. These purified phage were converted to plasmids by infecting Cre expressing hosts (BM25.8) according to the protocol provided with the lambda TriplEx vector (Clontech). Sequencing was carried out using ABI BigDye sequencing reagents.

Sequencing and Analysis

Sequencing templates were prepared using QIAprep mini spin columns according to the manufacturer's instructions. Both ends of clone all clones were sequenced using the following vector primers; TCCGAGATCTGGACGAGC (sense primer) (SED ID NO: 1) and TAATACGACTCAC-TATAGGG (anti-sense primer) (SED ID NO:2). Sequences were analyzed using BLASTn searches against NCBI (http://www.ncbi.nlm.nih.gov/).nr, EST and Unigene databases.

Production of Tumor Associated Antigens for Sandwich ELISAs

Recombinant histidine-tagged versions of the tumor associated antigens are produced. The histidine tag (or "His tag") contains 6 tandem histidine residues typically placed at the N- or C-terminus of the protein of interest. These 6 His residues allow binding of protein to metal conjugated ELISA plates. If necessary, these proteins can be further purified prior to ELISA by metal chelate chromatography.

To produce His tagged versions of the tumor associated antigens, cDNA clones encoding the complete open reading frame of a tumor associated antigen are obtained or assembled. Once full-length cDNAs corresponding to the antigens of interest are sequenced, they are inserted into the mammalian expression vector pcDNA3.1/His (Invitrogen) or the bacterial expression vector pQE (Quiagen) and sequenced. These vectors fuse six histidine residues to the recombinant protein. The resulting pcDNA plasmids are transiently transfected into COS7 cells (a green monkey kidney cell line) using LIPOFECTAMINE™. The pQE constructs are transformed into the E. coli strain XL1-Blu using standard Calcium Phosphate transformation protocols. Expression of the recombinant antigens is assessed by Western blot of whole-cell lysates using an antibody to the His tag (Clontech); cells transfected with an empty His vector serve as a negative controls.

ELISA Protocol

Serum antibodies to tumor antigens are detected by ELISA. 96-well Ni-NTA HisSorb Plates ELISA plates (Quiagen) are incubated for 2 hours at 20° C. with an optimized solution of his-tagged antigen containing cellular lysate. After incubation, plates are washed with PBS/0.5% Tween-20 and then incubated with human serum samples diluted 1:25, 1:50, 1:100, and 1:200 (extended titration assays is performed for sera which does not titer at 1:200). All serum samples are diluted 1:50 in PBS/1% BSA/1% FBS (fetal bovine serum)/25 µg/ml mouse IgG/0.01% $NaN_3$ and then serially in PBS/1% BSA. Serum samples from cancer patients and normal controls are tested in duplicate. 50 µl of diluted serum is added per ELISA well for one hour at room temperature. After washing with PBS/1% BSA, goat anti-human antibody conjugated to horseradish peroxidase (HRP) is added to wells at a 1:5000 dilution in PBS/1% BSA and incubated for 45 min at room temperature and washed. Experiments are carried out using two different isotype specific secondary antibodies specific for human IgG and IgA. After washing plates with PBS/1% BSA, the developing reagent TMB (Kirkegaard and Perry Laboratories, Gaithersburg Md.) is added. The color reaction is monitored at 640 nm until the wells coated with 14 nanogram human Ig reach an optical density (OD) of 0.3, at which point the reaction is stopped by adding 1N HCl. Plates are read at 450 nm by an automated plate reader.

Example 2

The following Table 1 summarizes the results of the screening described in Example 1. Shown are the results for 31 ovarian cancer patients whose serum was tested for the presence of autoimmune antibodies to the antigens indicated in each column. All antigens tested negative against a panel of 20 sera from age-matched disease-free females. "XX" denotes sera that are clearly positive by SEREX methodology for autoimmune antibodies to a given antigen. "©" indicates screening serum, usually from a pool of two patients. "E++" indicates a positive result by ELISA. "ND" indicates the ELISA was not developed. Empty cells indicate no reactivity.

TABLE 1

| Patient Number | Stage of Disease | ESO | Ubiquilin-1 | IFI 27 | P53 | HOX-B6 | ILF3 | ZFP161 | YB-1 | KIAA0136 | CD44 | Osteonectin | F-box prtn |
|---|---|---|---|---|---|---|---|---|---|---|---|---|---|
| 1 | IIIC | | | | | | | | | | | | © |
| 2 | IVA | | | | | | | | | | | | |
| 3 | IIIC | | | | | | | | | | | XX | XX © |
| 4 | IIIC | | | | XX © | | | XX © E++ | | | | | |

TABLE 1-continued

| Patient Number | Stage of Disease | ESO | Ubiquilin-1 | IFI 27 | P53 | HOX-B6 | ILF3 | ZFP161 | YB-1 | KIAA0136 | CD44 | Osteo-nectin | F-box prtn |
|---|---|---|---|---|---|---|---|---|---|---|---|---|---|
| 5 | IIIC | | | | | | | | | | | | |
| 6 | IIIC | | | | | | | | | | | | |
| 7 | IIIC | | | | | | | | | | XX © | | |
| 8 | IIIC | XX | XX E++ | | | | | | | | | | |
| 9 | IIIC | | | | | | | | | | | | |
| 10 | IVA | | | | | | | | | | © | | |
| 11 | I/II | | | | | | | | | | | | |
| 12 | I/II | | | | | | | | | | | | |
| 13 | IVA | | | | | | | | | | | | |
| 14 | I/II | | | | | | | | | | | | |
| 15 | IIIC | | | | | | | | | | | | |
| 16 | IIIC | | | | | XX E++ | | | | | | | |
| 17 | IVB | XX E++ | | | | | | | | | | | |
| 18 | IIIC | © | | | | | | | | | | | |
| 19 | IIIC | | | | | | | | | | | | |
| 20 | IIIC | | | © | | | | | | | | | |
| 21 | IIIC | | XX | | | | | | | | | | |
| 22 | I/II | | | | | | | | | | | | |
| 23 | IIIC | XX © E++ | | | | | | | | | | | |
| 24 | IVA | | © | | | XX © | | | © | | | | |
| 25 | IIIC | XX E++ | XX E++ © | | | © | | | XX © | | | | |
| 26 | IIIC | | | | | | XX © | | | | | | |
| 27 | IIIC | | | | | | © | | | | | | |
| 28 | I/II | | | | | | | | | | | | |
| 29 | IIIC | | | © | | | | | | | | | |
| 30 | IIIC | XX E++ | XX | | | | | | | | | | |
| 31 | | | | XX © | | | | | | © | | | |
| Serex | | 5 | 4 | 2 | 2 | 1 | 1 | 1 | 1 | 1 | 1 | 1 | 1 |
| ELISA ++ | | 4 | 2 | ND | 1 | ND | ND | 1 | ND | ND | ND | ND | ND |
| TOTAL | | 5 | 4 | 2 | 2 | 1 | 1 | 1 | 1 | 1 | 1 | 1 | 1 |

The previous examples are provided to illustrate but not to limit the scope of the claimed inventions. Other variants of the inventions will be readily apparent to those of ordinary skill in the art and encompassed by the appended claims. All publications, patents, patent applications and other references cited herein are hereby incorporated by reference.

What is claimed is:

1. A method for diagnosis of cancer in a subject, comprising:
    obtaining a sample from the subject, the sample comprising antibodies;
    contacting the sample with at least one tumor associated polypeptide antigen, the tumor associated antigen selected from the group consisting of
    (a) ZFP161,
    (b) Ubiquilin-1,
    (c) HOX-B6,
    (d) YB-1,
    (e) Osteonectin,
    (f) ILF3, and
    (g) a polypeptide comprising an antigenic fragment of any (a) through (f); and
    detecting complex formation between the tumor associated antigen and the antibodies in the sample; wherein complex formation indicates a diagnosis of a cancer.

2. The method of claim 1, wherein the subject is a mammal.

3. The method of claim 2, wherein the subject is human.

4. The method of claim 1, wherein the sample is blood, serum, ascites fluid, mucosal fluid, cervical wash, nipple aspirate fluid, stool, urine, saliva, tears, or sputum.

5. The method of claim 4, wherein the sample comprises serum.

6. The method of claim 1, wherein the detecting is by Western blot, radioimmunoassay, ELISA, sandwich immunoassay, immunoprecipitation assay, precipitin reaction, gel diffusion precipitin reaction, immunodiffusion assay, agglutination assay, complement-fixation assay, immunoradiometric assay, fluorescent immunoassay or protein A immunoassay.

7. The method of claim 1, wherein the cancer is epithelial cancer.

8. The method of claim 7, wherein the epithelial cancer is ovarian cancer, breast cancer, lung cancer or colorectal cancer.

9. The method of claim 1, further comprising:
    comparing the complex formation between the tumor associated antigen and the antibodies in the sample with complex formation of a standard to determine the diagnosis of the cancer.

* * * * *